US011844766B2

United States Patent
Labovitiadi et al.

(10) Patent No.: US 11,844,766 B2
(45) Date of Patent: *Dec. 19, 2023

(54) EXPEC GLYCOCONJUGATE VACCINE FORMULATIONS

(71) Applicant: Janssen Pharmaceuticals, Inc., Titusville, NJ (US)

(72) Inventors: Olga Labovitiadi, Oegstgeest (NL); Wouter Frank Tonnis, Berlin (DE); Francesco Doro, Siena (IT); Janik Adriaansen, The Hague (NL)

(73) Assignee: JANSSEN PHARMACEUTICALS, INC., Titusville, NJ (US)

( * ) Notice: Subject to any disclaimer, the term of this patent is extended or adjusted under 35 U.S.C. 154(b) by 138 days.

This patent is subject to a terminal disclaimer.

(21) Appl. No.: 17/318,616

(22) Filed: May 12, 2021

(65) Prior Publication Data

US 2021/0275681 A1 Sep. 9, 2021

Related U.S. Application Data

(63) Continuation of application No. 16/709,223, filed on Dec. 10, 2019, now Pat. No. 11,033,633, which is a continuation of application No. 16/191,659, filed on Nov. 15, 2018, now Pat. No. 10,525,145, which is a continuation of application No. 15/792,242, filed on Oct. 24, 2017, now Pat. No. 10,159,751.

(30) Foreign Application Priority Data

Oct. 24, 2016 (EP) ..................... 16195256

(51) Int. Cl.
| | | |
|---|---|---|
| *A61K 47/64* | (2017.01) | |
| *C08B 37/00* | (2006.01) | |
| *A61K 47/65* | (2017.01) | |
| *A61K 39/108* | (2006.01) | |
| *A61K 47/02* | (2006.01) | |
| *A61K 47/20* | (2006.01) | |
| *A61K 47/26* | (2006.01) | |
| *A61K 39/00* | (2006.01) | |

(52) U.S. Cl.
CPC ........ *A61K 47/646* (2017.08); *A61K 39/0258* (2013.01); *A61K 47/02* (2013.01); *A61K 47/20* (2013.01); *A61K 47/26* (2013.01); *A61K 47/6415* (2017.08); *A61K 47/65* (2017.08); *C08B 37/0063* (2013.01); *A61K 2039/55511* (2013.01); *A61K 2039/55583* (2013.01); *A61K 2039/6037* (2013.01); *A61K 2039/6087* (2013.01); *A61K 2039/70* (2013.01); *A61K 2300/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 3,700,612 A | 10/1972 | Joseph |
| 5,057,540 A | 10/1991 | Kensil |
| 5,370,872 A | 12/1994 | Cryz |
| 6,331,415 B1 | 12/2001 | Cabilly |
| 6,858,211 B1 | 2/2005 | Szu |
| 9,700,612 B2 | 7/2017 | Kowarik |
| 9,849,169 B2 | 12/2017 | Nagy |
| 10,150,952 B2 | 12/2018 | Haas |
| 10,159,751 B2 | 12/2018 | Labovitiadi |
| 10,206,992 B2 | 2/2019 | Nagy |
| 10,441,647 B2 | 10/2019 | Kowarik |
| 10,525,145 B2 | 1/2020 | Labovitiadi |
| 10,577,592 B2 | 3/2020 | Haas |
| 10,583,185 B2 | 3/2020 | Poolman |
| 10,940,191 B2 | 3/2021 | Nagy |
| 10,940,192 B2 | 3/2021 | Kowarik |
| 11,015,177 B2 | 5/2021 | Haas |
| 11,033,633 B2 | 6/2021 | Labovitiadi |
| 11,446,370 B2 | 9/2022 | Geurtsen |
| 2014/0038296 A1 | 2/2014 | Palsson |
| 2015/0238588 A1 | 8/2015 | Kowarik |
| 2018/0002679 A1 | 1/2018 | Haas |
| 2019/0078064 A1 | 3/2019 | Haas |
| 2020/0181586 A1 | 6/2020 | Haas |
| 2020/0316184 A1 | 10/2020 | Geurtsen |
| 2020/0353073 A1 | 11/2020 | Geurtsen |
| 2021/0154286 A1 | 5/2021 | Kowarik |

FOREIGN PATENT DOCUMENTS

| | | |
|---|---|---|
| CN | 101983070 | 3/2011 |
| EP | 2289911 | 3/2011 |
| GB | 2220211 A | 1/1990 |
| JP | S62500173 | 1/1987 |
| JP | H10500102 A | 1/1998 |

(Continued)

OTHER PUBLICATIONS

Poolman, J.T., et al, "The history of pneumococcal conjugate vaccines development: dose selection," Expert Reviews Vaccines, vol. 12 (12), pp. 1379-1394 (2013).

(Continued)

*Primary Examiner* — Brian Gangle
(74) *Attorney, Agent, or Firm* — ICE MILLER LLP

(57) ABSTRACT

Compositions and methods for inducing an immune response against extra-intestinal pathogenic *Escherichia coli* (ExPEC) are described. In particular, multivalent vaccines containing O-antigen polysaccharide covalently bound to an exotoxin A of *Pseudomonas aeruginosa* (EPA) carrier protein that can withstand multiple environmental stresses are describe.

22 Claims, 5 Drawing Sheets

Specification includes a Sequence Listing.

(56) References Cited

FOREIGN PATENT DOCUMENTS

| | | |
|---|---|---|
| JP | 2004515450 A | 5/2004 |
| JP | 2007256214 | 10/2007 |
| JP | 2008539743 A | 11/2008 |
| JP | 2011514155 | 5/2011 |
| JP | 4791866 B2 | 10/2011 |
| JP | 2012525376 A | 10/2012 |
| JP | 2017507178 | 3/2017 |
| JP | 2018525423 A | 9/2018 |
| RU | 2189253 C1 | 9/2002 |
| WO | 8601806 A1 | 3/1986 |
| WO | 86001806 | 3/1986 |
| WO | 9303765 A1 | 3/1993 |
| WO | 9522563 A1 | 8/1995 |
| WO | 9523256 | 8/1995 |
| WO | 2001078787 A2 | 10/2001 |
| WO | 2003074679 | 9/2003 |
| WO | 2003074687 A1 | 9/2003 |
| WO | 2004078209 A1 | 9/2004 |
| WO | 2006119987 A2 | 11/2006 |
| WO | 2007109812 A2 | 9/2007 |
| WO | 2007109813 A1 | 9/2007 |
| WO | 2009036379 | 3/2009 |
| WO | 2009089396 A2 | 7/2009 |
| WO | 2009104074 A2 | 8/2009 |
| WO | 2010105256 | 9/2010 |
| WO | 2010125565 A2 | 11/2010 |
| WO | 2011062615 | 5/2011 |
| WO | 2012009568 | 1/2012 |
| WO | 2012078482 A1 | 6/2012 |
| WO | 2013034664 A1 | 3/2013 |
| WO | 2014037585 A1 | 3/2014 |
| WO | 2014057109 A1 | 4/2014 |
| WO | 2014102265 A1 | 7/2014 |
| WO | 2014111516 A1 | 7/2014 |
| WO | 2015052344 | 4/2015 |
| WO | 2015117711 A1 | 8/2015 |
| WO | 2015124769 A1 | 8/2015 |
| WO | 2016107818 A1 | 7/2016 |
| WO | 2016107819 A1 | 7/2016 |
| WO | 2017035181 A1 | 3/2017 |
| WO | 2018077853 A1 | 5/2018 |
| WO | 2019016187 A1 | 1/2019 |
| WO | 2020191082 | 9/2020 |
| WO | 2020191088 | 9/2020 |

OTHER PUBLICATIONS

Abbanat et al., Poster presented at ASM's Interscience Conference of Antimicrobial Agents and Chemotherapy (ICAAC), Jun. 16-20, 2016, Boston, 1 page.

Angela M. Giusti, et al., "Somatic diversification of S107 from an antiphosphocholine to an anti-DNA autoantibody is due to a single base change in its heavy chain variable region", in Proc. Natl. Acad. Sci., vol. 84, May 1987, pp. 2926-2930 (5 pgs.).

Angela Novais, et al., "Contribution of IncFII and Broad-Host IncA/C and IncN Plasmids to the Local Expansion and Diversification of Phylogroup B2 Escherichia coli ST131 Clones Carrying blaCTX-M-15 and qnrS1 Genes", in Antimicrobial Agents and Chemotherapy, vol. 56, No. 5, May 2012, pp. 2763-2766 (4 pgs.).

Arturo Casadevall, et al., "Immunoglobulin isotype influences affinity and specificity", in PNAS, vol. 109, No. 31, Jul. 31, 2012, pp. 12272-12273 (2 pgs.).

B.R. Brodeur et al., "Mouse-Human Myeloma Partners for the Production of Heterohybridomas", Monoclonal Antibody Production Techniques and Applications, Marcel Dekker, Inc., 1987, pp. 51-63.

Brown et al., "Tolerance to Single, but Not Multiple, Amino Acid Replacements in Antibody Vh CDR2," The Journal of Immunology, 1996, 156: 3285-3291.

Chris Galanos, et al., "Galactosamine-induced sensitization to the lethal effects of endotoxin", in Proc. Natl. Acad. Sci., vol. 76, No. 11, Nov. 1979, pp. 599-5943 (5 pgs.).

Claudia Sheedy, et al., "Isolation and affinity maturation of hapten-specific antibodies", in Biotechnolgy Advances 25, 2007, pp. 333-352 (20 pgs.).

ClinicalTrials.gov archive, "History of Changes for Study: NCT03819049, A Study of Three Different Doses of VAC52416 (ExPEC10V) in Adults Aged 60 to 85 Years in Stable Health", htt;s://clinicaltrials.gov/ct2/history/NCT03819049, Aug. 6, 2019 (v6), 6 pages.

Cristina Caldas, et al., "Humanization of the anti-CD18 antibody 6.7: an unexpected effect of a framework residue in binding to antigen", in Molecular Immunology, vol. 39, 2003, pp. 941-952 (12 pgs.).

D. Kozbor et al., "A Human Hybrid Myeloma for Production of Human Monoclonal Antibodies", The Journal of Immunology, Dec. 1984, vol. 133, No. 6, pp. 3001-3005.

DebRoy C, Fratamico PM, Yan X, Baranzoni G, Liu Y, et al. (2016) Correction: Comparison of O-Antigen Gene Clusters of All O-Serogroups of Escherichia coli and Proposal for Adopting a New Nomenclature for O-Typing. PLOS ONE 11(4): e0154551, Published: Apr. 27, 2016, 5 pages.

DebRoy et al., "Comparison of O-Antigen Gene Clusters of All O-Serogroups of Escherichia coli and Proposal for Adopting a New Nomenclature for O-Typing," PLoS ONE 11(1): e0147434, Jan. 29, 2016, 13 pages.

Denka Seiken Co. Ltd.(Catalogue), Bacterial Antisera "SEIKEN", [DENKA SEIKEN Co.,Ltd, MSDS No. 200000-01, Feb. 16, 2010. 13 pages.

Duda et al., "The lipopolysaccharide of the mastitis isolate Escherichia coli strain 1303 comprises a novel O-antigen and the rare K-12 core type," Microbiology (2011), 157, 1750-1760, doi: 10.1099/mic.0.046912-0.

European Office Action dated Mar. 7, 2017, in connection with corresponding EP Application No. 14703783.2 (7 pgs.).

European Search Report issued in International Application No. 13151627.0 dated Mar. 28, 2013. 7 pages.

Extended European Search Report dated Jul. 16, 2014, in connection with corresponding EP Application No. 4154158.1 (5 pgs.).

Extended European Search Report dated Mar. 14, 2017, including the European Search Report and the European Search Opinion, in connection with corresponding EP Application No. 16201732.1 (10 pgs.).

Extended Search Report dated Sep. 10, 2021 in EP Application No. 21154782.3, 6 pages.

G. Kohler et al., "Continuous cultures of fused cells secreting antibody of predefined specificity", Nature, Aug. 7, 1975, vol. 256, pp. 495-497.

G. Peirano, et al., "Molecular characteristics of extended-spectrum β-lactamase-producing Escherichia coli from the Chicago area: high prevalence of ST131 producing CTX-M-15 in community hospitals", International Journal of Antimicrobial Agents, 2010, vol. 36, pp. 19-23.

G. Peirano, et al., "Molecular epidemiology of Escherichia coli producing CTX-M beta-lactamases: the worldwide emergence of clone ST131 O25:H4", in International Journal of Antimicrobial Agents, vol. 35, 2010, pp. 316-321 (7 pgs.).

Gisele Peirano, et al., "Characteristics of Escherichia coli Sequence Type 131 Isolates That Produce Extended-Spectrum B-Lactamases: Global Distribution of the H30-Rx Sublineage", in Antimicrobial Agents and Chemotherapy, vol. 58, No. 7, Jul. 2014, pp. 3762-3767 (6 pgs.).

Helen Miajlovic, et al., "Response of Extraintestinal Pathognenic Escherichia coli to Human Serum Reveals a Protective Role for Rcs-Regulated Exopolysaccharide", in Infection and Immunity, vol. 82, No. 1, Jan. 2014, pp. 298-305 (8 pgs.).

Huttner et al., "Safety, immunogenicity, and preliminary clinical efficacy of a vaccine against extraintestinal pathogenic Escherichia coli in women with a history of recurrent urinary tract infection: a randomised, single-blind, placebo-controlled phase 1b trial", Lancet Infect Dis., 2017, vol. 17, No. 5, pp. 528-537.

Ihssen Julian et al., "Production of glycoprotein vaccines in Escherichia coli", Microbial Cell Factories,, (2010), vol. 9, No. 1, doi:10.1186/1475-2859-9-61, ISSN 1475-2859, p. 61, XP021077209.

(56) References Cited

OTHER PUBLICATIONS

International Search Report and Written Opinion issued in International Application No. PCT/EP2014/078709 dated May 12, 2015, 4 pages.
International Search Report issued in International Application No. PCT/EP2014/050895 dated Mar. 14, 2014. 2 pages.
International Search Report dated Jun. 12, 2020 in PCT/US2020/023404, 5 pages.
J. Wibbenmeyer et al., "Cloning, expression, and characterization of the Fab fragment of the anti-lysozyme antibody HyHEL-5", Biochimica et Biophysica Acta, 1999, vol. 1430, No. 2, pp. 191-202.
Jansson et al., "Sturctural Studies of the O-Antigen Polysaccharide of *Escherichia coli* O4", Carbohydrate Research, 134 (1984) 283-291.
Jeffrey Skolnick, et al., "From genes to protein structure and function: novel applications of computational approaches in the genomic era", in TIBTECH, vol. 18, Jan. 2000, pp. 34-39 (6 pgs.).
Josef Prassler, et al., "In vitro affinity maturation of HuCAL antibodies: complementarity determining region exchange and RapMat technology", in Immunotherapy, vol. 1, No. 4, 2009, pp. 571-583 (13 pgs.).
Marie-Paule Lefranc, et al., "IMGT, the international ImMunoGeneTics database", in Nucleic Acids Research, vol. 27, No. 1, 1999, pp. 209-212 (4 pgs.).
Myung-Hoon Lee, et al., "Expression and functional reconstitution of a recombinant antibody (Fab') specific for human apolipoprotein B-100", Journal of Biotechnology, 2003, vol. 101, pp. 189-198.
N. Woodford et al., "Multiresistant Gram-negative bacteria: the role of high-risk clones in the dissemination of antibiotic resistance", FEMS Microbiol Rev, 2011, vol. 35, No. 5, pp. 736-755.
Nadine C. Chien, et al., "Significant structural and functional change of an antigen-binding site by a distant amino acid substitution: Proposal of a structural mechanism", in Proc. Natl. Acad. Sci., vol. 86, Jul. 1989, pp. 5532-5536 (5 pgs.).
Nagy, Gábor and Pál, Tibor. "Lipopolysaccharide: a tool and target in enterobacterial vaccine development" , vol. 389, No. 5, 2008, pp. 513-520, downloaded from the Internet https://www.degruyter.com/document/doi/10.1515/BC.2008.056/html.
Neil S. Greenspan, et al., "Defining epitopes: It's not as easy as it seems", in Nature Biotechnology, vol. 17, Oct. 1999, pp. 936-937 (2 pgs.).
Notification Concerning Transmittal of International Preliminary Report on Patentability dated Aug. 18, 2016, in connection with corresponding international Application No. PCT/EP2014/078709 (7 pgs.).
Office Action dated Mar. 29, 2018 in Russian Patent Application No. 2015134413, with English translation. 12 pages.
Office Action dated Oct. 17, 2018 in corresponding Russian Application No. 2015134413/10(052839), 17 pages including English-language translation.
Office Action dated Apr. 22, 2021 in corresponding Russian Patent Application No. 2019144146/10(085375), 9 pages, with English Translation.
Office Action dated Aug. 23, 2018 in corresponding Russian Application No. 2016135962, 17 pages including English-language translation.
Office Action dated Aug. 28, 2018 in corresponding Japanese Application No. 2015-553093; 12 pages including English-language translation.
Office Action dated Oct. 4, 2018 in corresponding Japanese Application No. 2016-550556; 9 pages including English-language translation.
Pablo Umaña, et al., "Engineeredglycoforms of an antineuroblastoma IgG1 with optimized antibody-dependent cellular cyto9toxic activity", in Nature Biotechnology, vol. 17, Feb. 1999, pp. 176-180 (5 pgs.).
Pinayev et al., "The Cell Cultures", Information Gazette, 2010, Issue 26, St. Petersburg, 61 pages.
Reschedko, G.K. et al, "*Escherichia coli*as a Nosocomial Pathogen in ICUs", Clinical microbiology and antimicrobial chemotherapy, 2011, vol. 13, No. 4, pp. 314-321.
Response to Austrian Office Action dated Mar. 12, 2019 in Austrian Patent Application No. 2018204437. 6 pages.
Roland Stenutz et al, "The structures of*Escherichia coli* O-polysaccharide antigens", FEMS Microbiology Reviews, Elsevier, Amsterdam; NL, vol. 30, doi:10.1111/J.1574-6976.2006.00016.X, ISSN 0168-6445, (Jan. 1, 2006), pp. 382-403, (Feb. 9, 2006), XP007921666.
Royt A et al., "Hypervariable sequences of antigen-recognition centers enable binding of various antigens by antibodies", Immunology, Moscow, "Mir" Publishers 2000, 4 pages including English-language translation, abstract only.
Russian Office Action dated Apr. 24, 2018, in connection with corresponding RU Application No. 2016135962/10 (056446) (5 pgs.).
Russian Office Action dated Dec. 27, 2017, in connection with corresponding RU Application No. 2015134413/10 (052839) (18 pgs., including English translation).
S. Muller-Loennies, et al., "Structural Analysis of Oligosaccharides from Lipopolysaccharide (LPS) of *Escherichia coli* K12 Strain W3100 Reveals a Link between Inner and Outer Core LPS Biosynthesis", The Journal of Biological Chemistry, Sep. 5, 2003, vol. 278, No. 36, pp. 34090-34101.
Saade, Elie, et al., "Characertization of *Escherichia coli* isolates potentially covered by ExPEC4V and ExPEC10V, that were collected from post-transrectal ultrasound-guided prostate needle biopsy," Vasccine, Elsevier, Amsterdam, NL, vol. 38, No. 33, Jun. 16, 2020 pp. 5100-5104.
Simone Cagnacci, et al., "European Emergence of Ciprofloxacin-Resistant *Escherichia coli* Clonal Groups O25:H4-ST131 and 015:K52:H1 Causing Community-Acquired Uncomplicated Cystitis", in the Journal of Clinical Microbiology, Aug. 2008, vol. 46, No. 8, pp. 2605-2612 (8 pgs.).
Szijarto et al., "Bactericidal Monoclonal Antibodies Specific to the Lipopolysaccharide 0 Antigen from Multidrug-Resistant *Escherichia coli* Clone ST131-025b:H4 Elicit Protection in Mice," Antimicrobial Agents and Chemotherapy, Jun. 2015, vol. 59, No. 6, pp. 3109-3116, XP009187151.
Vajdos et al., "Comprehensive Functional Maps of the Antigen-binding Site of an Anti-ErbB2 Antibody Obtained with Shotgun Scanning Mutagenesis," J Mol. Biol. 2002, vol. 320(2), pp. 415-428.
Van Den Dobbelsteen Germie P J M et al, "Immunogenicity and safety of a tetravalent*E. coli*O-antigen bioconjugate vaccine in animal models", Vaccine, Elsevier, Amsterdam, NL, (Jul. 6, 2016), vol. 34, No. 35, doi:10.1016/J.VACCINE.2016.06.067, ISSN 0264-410X, pp. 4152-4160, XP029644969.
Wacker, M., et al., "Substrate specificity of bacterial oliogsaccharyltransferase suggests a common transfer mechanism for the bacterial and eukaryotic systems," PNAS, vol. 103, No. 18, pp. 7088-7093, May 2, 2006.
Written Opinion dated Jun. 12, 2020 in PCT/US2020/023404, 6 pages.
Written Opinion of the International Searching Authority dated Mar. 14, 2014, in connection with corresponding International Application No. PCT/EP2014/050895. 8 pages.
Yakubke et al., "Amino acids, peptides, proteins", MTR Publishers, 1985, 456 pages.
"Typhoid Vi Polysaccharide Vaccine Typhim VI," Sanofi Pasteur Inc., vol. 3., pp. 1-26 (Mar. 2014).
A. Cross et al, "Safety And Immunogenicity Of A Polyvalent *Escherichia coli* Vacsine In Human Volunteers", Journal of Infectious Diseases. JID, Chicago, IL, (1994), vol. 170, No. 4, doi:10.1093/infdis/170.4.834, ISSN 0022-1899, pp. 834-840, XP055311603.
Amor et al., "Distribution of core oligosaccharide types in lipopolysaccharides from *Escherichia coli*," Infect. Immun., vol. 68, No. 3, pp. 1116-1124 (2000).
Banerjee et al., "A new clone sweeps clean: the enigmatic emergence of *Escherichia coli* sequence type 131," Antimicrob Agents Chemother. vol. 58, No. 9, pp. 4997-5004 (2014).

(56) References Cited

OTHER PUBLICATIONS

Blanco et al., "Virulence factors and 0 groups of *Escherichia coli* isolates from patients with acute pyelonephritis, cystitis and asymptomatic bacteriuria," Eur. J. Epidemiol., vol. 12, No. 2, pp. 191-198 (1996).
Blanco et al.,"Molecular epidemiology of *Escherichia coli* producing extended-spectrum {beta}—lactamases in Lugo (Spain): dissemination of clone O25b:H4-ST131 producing CTX-M-15," J. Antimicrob. Chemother., vol. 63, pp. 1135-1141 (2009).
Bowie etal. (Science, 1990, 247:1306-1310).
Burgess et al. (J. Cell Biol. 111:2129-2138, 1990).
Clermont et al,"The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Clermont et al., "Rapid Detection of the O25b-ST131 clone of *Escherichia coil* encompassing the CTX-M-15- producing strains," Journal of Antimicrobial Chemotherapy, vol. 64, No. 2, pp. 274-277 (2009).
Cryz Jr. et al., "Synthesis and Characterization of *Escherichia coli* O18 O-Polysaccharide Conjugate Vaccines," Infection and Immunity, vol. 58, No. 2, pp. 373-377 (1990).
Cryz S J et al, "Synthesis and characterization of a polyvalent *Escherichia coli* O-polysaccharide-toxin A conjugate vaccine", Vaccine, Elsevier Ltd, GB, (1995), vol. 13, No. 5, doi:10.1016/0264-410X(94)00009-C, ISSN 0264-410X, pp. 449-453, XP004057719.
Datsenko et al., "One-step inactivation of chromosomal genes in *Escherichia coli* K-12 using PCR products," PNAS, vol. 97, No. 12, pp. 6640-6645 (2000).
Debroy et al., "Detection of O antigens in *Escherichia coli*," Animal Health Research Reviews, vol. 12, No. 2, pp. 169-185 (2011).
Extended Search Report dated Apr. 12, 2017 in EP Application No. 16195256.9, 8 pages.
Foxman, "Epidemiology of Urinary Tract Infections: Incidence, morbidity, and Economic Costs", The American Journal of Medicine, vol. 113(1A), 5S-13S, Jul. 2002.
Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).
Frenck, et al., "Safety and Immunogenicity of a vaccine for extraintestinal pathogenic *Escherichia coli* (ESTELLA): a phase 2 randomised controlled trial," Lancet Infect. Dis. vol. 1, No. 6, pp. 631-640 (2019).
Fundin et al., "NMR analysis of the O-antigen polysaccharide from *Escherichia coli* strain F171," Magnetic Resonance in Chemistry, vol. 41, No. 3, pp. 202-205 (2003).
Glover et al., "Chemoenzymatic synthesis of Glycopeptides with PgIB, a bacterial oligosaccharyl transferase from Campylobacter jejuni," Chemistry and Biology, Current Biology, vol. 12, No. 12, pp. 1311-1316 (2005).
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Ihssen et al., "Production of glycoprotein vaccines in *Escherichia coli*," Microbial Cell Factories, vol. 9, No. 61, pp. 1-13 (2010).
Int'l Preminary Report on Patentability dated Feb. 14, 2019 in Int'l Application No. PCT/EP2017/077123, 16 pages.
Int'l Search Report and Written Opinion dated Jul. 20, 2017 in Int'l Application No. PCT/US2016/048278, 9 pages.
Int'l Search Report and Written Opinion dated Jun. 15, 2015 in Int'l Application No. PCT/EP2015/053739, 10 pages.
Int'l Search Report and Written Opinion dated Oct. 27, 2016 in Int'l Application No. PCT/US2016/048278, 16 pages.
Int'l Search Report dated Jan. 24, 2018 in Int'l Application No. PCT/EP2017/077123, 6 pages.
International Search Report and Written Opinion for App. No. PCT/US2020/023415, dated Jun. 12, 2020, 21 pages.
Jadhav et al., "Virulence characteristics and genetic affinities of multiple drug resistant uropathogenic *Escherichia coli* from a Semi Urban Locality in India," PLOS One, vol. 6, No. 3, (2011), 7 pages.

Jann et al., "Structural Comparison of the O6 Specific Polysaccharides From *Escherichia coli* O6:K2:H1, *Escherichia coli* O6:K13:H1, and *Escherichia coli* O6:K54:H10," Carbohydrate Research, vol. 263, No. 2, pp. 217-225 (1994).
Jansson et al., "Structural studies of the *Escherichia coli* O-antigen 6," Carbohydrate Research, vol. 131, No. 2, pp. 277-283 (1984).
Jansson et al., "Structural studies of the O-specific side-chains of the *Escherichia coli* O2 lipopolysaccharide," Carbohydrate Res., vol. 161, pp. 273-279 (1987).
Jiang et al., "Tungsten-Induced Protein Aggregation: Solution Behavior," Wiley InterScience, vol. 98, No. 12, pp. 4695-4710 (2009).
Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).
Johnson et al., Extraintestinal Pathogenic *Escherichi coli*: "The other bad *E coli*", J Lab Clin Med., 139(3), pp. 155-162, 2002.
Kenne et al., "Structural studies of the *Escherichia coli* O-antigen 25," Carbohydrate Research, vol. 122, No. 2, pp. 249-256 (1983).
Kim et al., "Efficiency of a pneumococal Opsonophagocytic Killing Assay Improved by Multiplexing and by Colloring Colonies", Clinical and Dianostic laboratory Immunology, pp. 616-621, Jul. 2003.
Kohler et al., "What defines extraintestinal pathogenic *Escherichia coli*", Elsevier, International journal of Medical Microbiology 301, pp. 642-647, 2011.
Laurentin et al., "A Microtiter Modification of the anthrone-sulfuric acid colorimetric assay for glucose-based carbohydrates", Analytical Biochemistry, 315, pp. 143-145, 2003.
Lazar et al. (Mol. Cell. Biol., 8:1247-1252, 1988).
Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999, 10 pages.
Lukac et al., "Toxoid of Pseudomonas aeruginosa exotoxin A generated by deletion of an active-site residue," Infect Immun, vol. 56, No. 12, pp. 3095-3098 (1988).
Mario F Feldman et al, "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).
Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).
Mora et al., "Emergence of clonal groups O1:HNM-D-ST59, O15:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain," International J. of Antimicrob. Agents, vol. 37, No. 1, pp. 16-21 (2011).
Phan et al., "The serum resistome of a globally disseminated multidrug resistant uropathogenic *Escherichia coil* clone," PLOS Genetics, vol. 9, No. 10, pp. 1-18 (2013).
Pitout et al., "Extraintestinal Pathogenic *Escherichia coli*: An Update on Antimicrobial Resistance, Laboratory Diagnosis and Treatment," Expert Rev. Anti. Infect. Then, vol. 10, No. 10, pp. 1165-1176 (2012).
Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).
Rogers B.A et al., "*Escherichia coli* O25b-ST131: a pandemic, multiresistant, community-associated strain", Journal of Antimicrobial Chemotherapy, 2011, vol. 66, No. 1, pp. 1-14.
Russo et al., "A killed, genetically engineered derivative of a wild-type extraintestinal pathogenic *E coli* strain is a caccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
Schito et al., "The ARESC study: an international survey on the antimicrobial resistance of pathogens involved in uncomplicated

(56) References Cited

OTHER PUBLICATIONS urinary tract infections", Elsevier, International Journal of Antimicrobial Agents 34, pp. 407-413, 2009.
Seidl et al., "Tungsten-Induced Denaturation and Aggregation of Epoetin Alfa During Primary Packaging as a Cause of Immunogenicity," Pharm. Res., vol. 29, pp. 1454-1467 (2012).
Stenutz R et al, "The structures of *Escherichia coli* O-polysaccharide antigens.", FEMS Microbiol Rev. May 2006;30(3):382-403.
Stevenson et al., "Structure of the O antigen of *Escherichia coli* K-12 and the sequence of its rfb gene cluster," J. Bacteriol., vol. 176, No. 13, pp. 4144-4156 (1994).
Stoute et al., "A Preliminary Evaluation of a Recombinant Circumsporozoite Protein Vaccine Against Plasmodium Falciparum Malaria," New England Journal of Medicine, vol. 336, pp. 86-91 (1997).
Szijarto et al. "The rapidly emerging ESBL-producing *Escherichia coil* O25-ST131 clone carries LPS core synthesis genes of the K-12 type," FEMS Microbiol. Lett., vol. 332, pp. 131-136 (2012).
Terai et al., "*Escherichia coli* Virulence Factors and Serotypes in Acute Bacterial Prostatitis," Int. Journal of Urology, vol. 4, No. 3, pp. 289-294 (1997).
V. Szijarto et al, "Diagnostic Potential of Monoclonal Antibodies Specific to the Unique O-Antigen of Multidrug-Resistant Epidemic *Escherichia coli* Clone ST131-O25b:H4", Clinical and Vaccine Immunology, (2014), vol. 21, No. 7, doi:10.1128/CVI.00685-13, ISSN 1556-6811, pp. 930-939, XP055179667.
Van Den Dobbelsteen et al.,"Immunogenicity and safety of tetravalent *Escherichia coli* O-antigen bioconjugate vaccine in animal models," Vaccine, vol. 34, No. 35, pp. 4152-4160 (2016).
Wacker et al., "N-linked glycosylation in Campylobacter jejuni and its functional transfer into *Escherichia coli*," Science, vol. 298, No. 5599, pp. 1790-1793 (2002).
Written Opinion dated Dec. 21, 2018 in Int'l Application No. PCT/EP2017/077123, 8 pages.
Written opinion of the Int'l Searching Authority dated Jan. 24, 2018 in Int'l Application No. PCT/EP2017/077123, 6 pages.
Written Opinion of the International Preliminary Examining Authority dated Sep. 11, 2018 in PCT/EP2017/077123, 8 pages.
Wu et al., "Pharmaceutics," Pharmacist Online (www.cmstpx.com), Red Editor. 2nd Edition.—Beijing: China Medical Science and Technology Press, 2013, 7 pages. English translation provided (8 pages).
Yuan et al., "Modern Pharmaceutical Technology, vol. 1," Modern Pharmaceutical Technology, vol. 1 / Edited by Yuan Yingjin—Beijing: Chemical Industry Press, May 2004, 5 pages. English translation provided (9 pages).

EXPEC GLYCOCONJUGATE VACCINE FORMULATIONS

CROSS-REFERENCE TO RELATED APPLICATIONS

This application is a continuation of U.S. application Ser. No. 16/709,223, filed Dec. 10, 2019, now allowed, which is a continuation of U.S. application Ser. No. 16/191,659, filed Nov. 15, 2018, now U.S. Pat. No. 10,525,145, which is a continuation of U.S. application Ser. No. 15/792,242, filed Oct. 24, 2017, now U.S. Pat. No. 10,159,751, which claims priority under 35 U.S.C. § 119 to European Application No. 16 195 256.9 filed on 24 Oct. 2016, the contents of all of which are hereby incorporated by reference in their entireties.

FIELD OF THE INVENTION

This invention relates to compositions for inducing an immune response against extra-intestinal pathogenic *Escherichia coli* (ExPEC). In particular, embodiments of this invention relate to multivalent vaccines containing conjugates of *E. coli* polysaccharide antigens covalently bound to a carrier protein that can withstand multiple environmental stresses.

REFERENCE TO SEQUENCE LISTING SUBMITTED ELECTRONICALLY

This application contains a sequence listing, which is submitted electronically via EFS-Web as an ASCII formatted sequence listing with a file name "004852.24US4_SL" and a creation date of May 3, 2021, and having a size of 6.2 KB. The sequence listing submitted via EFS-Web is part of the specification and is herein incorporated by reference in its entirety.

BACKGROUND OF THE INVENTION

Extra-intestinal pathogenic *E. coli* (ExPEC) is the most common gram-negative pathogen in humans, and can cause various infections outside of the gastrointestinal tract, which can lead to diverse and serious diseases, resulting in significant morbidity and mortality. Increasing multidrug resistance among ExPEC strains is an obstacle to treatment and leads to increasing numbers of hospitalizations and deaths and increasing healthcare costs associated with ExPEC infections.

A vaccine against ExPEC is therefore urgently needed. The O-antigen, a component of the surface lipopolysaccharide, has been identified as a promising vaccine target, and is used as antigen in a glycoconjugate vaccine that is currently under development (see, e.g. Poolman and Wacker, 2016, J. Infect. Dis. 213: 6-13).

The glycoconjugate vaccines against ExPEC that are currently under development comprise O-glycans of different serotypes of ExPEC, each coupled to a carrier protein, such as exoprotein A of *Pseudomonas aeruginosa* (EPA) (see e.g., WO2015/124769, and WO 2017/035181). Such a vaccine comprising O-glycans of the *E. coli* serotypes O25B, O1A, O2 and O6A is for instance in an ongoing phase 2 trial (ClinicalTrials.gov Identifier: NCT02546960).

It was found by the instant inventors that while the existing ExPEC vaccine formulation (25 mM Tris pH 7.4, 2.7 mM KCl, 137 mM NaCl) is acceptable for short-term storage at 2-8° C. and in-use stability, it is not robust upon freeze/thaw and under agitation stress. Accidental freezing, accidental heating, and agitation (e.g., during storage or transportation) has a detrimental impact on product integrity of the ExPEC formulations. For pharmaceutical products that are intended for use in large populations, such as a glycoconjugate vaccine against ExPEC, it is beneficial to have a formulation that can be frozen in bulk at low temperatures, and after thawing can be stored at about 2-8° C. before usage (i.e., where the drug substance is frozen for large scale and long term storage, but the drug product that is being used is stored at about 2-8° C., so at least one freeze-thaw cycle is inevitable for the product). Further, the formulation would preferably also be compatible with different materials, such that the product (e.g., the glycoconjugate) can be stored in different formats (e.g., bags, bottles, vials, prefilled syringes, and/or applicable devices).

There is a need in the art for formulations of vaccines against ExPEC, that can withstand multiple environmental stresses (e.g., freeze/thaw, agitation, elevated temperature, light exposure, metal oxidant exposure, etc.) and result in a longer stability and longer shelf life of the compositions, and preferably are compatible with multiple processing (e.g. container) materials. Any of the degradation routes resulting from an environmental stress can lead to lowered biological activity, and can potentially also result in the formation of by-products or derivatives of the components of the formulations, thus resulting in increased toxicity and/or altered immunogenicity of the ExPEC vaccine. Therefore, a tailored approach is needed to find a robust formulation for glycoconjugate vaccines ensuring stability over a wide range of conditions. Buffer type, pH, and specialized excipients will need to be selected, specifically combined, and subsequently meticulously optimized to keep glycoconjugate vaccines chemically, physically, and biologically stable. In view of all the factors that can vary, finding optimal conditions for formulating glycoconjugate vaccines against ExPEC is burdened with challenges, and the composition of a good formulation is a priori unpredictable.

Accordingly, there is a need in the art for formulations of glycoconjugate vaccines against ExPEC that ensure that the vaccine compositions can withstand multiple environmental stresses and have an improved stability and longer shelf life. It is the aim of the present invention to provide such formulations.

BRIEF SUMMARY OF THE INVENTION

Provided are two new formulations for glycoconjugate vaccines against ExPEC, providing the vaccine compositions with improved stabilizing effect upon freeze/thaw, agitation stress, thermal stress, and metal induced oxidation stress, which formulations are additionally compatible with various processing (e.g. container) materials. These improved formulations can be utilized during storage or transportation of both the drug product and the drug substance, where (accidental) freezing or harsh agitation can occur, which can have a detrimental impact on product integrity and therefore efficacy. Additionally, the novel formulations provided the glycoconjugate ExPEC vaccines with improved stability against thermal stress, and therefore can have a broad commercial application with respect to drug product and drug substance storage, handling and transportation in a wide range of temperatures and conditions.

Provided herein are compositions comprising at least one *E. coli* O antigen polysaccharide, wherein the at least one O antigen polysaccharide is covalently bound to a exotoxin A of *Pseudomonas aeruginosa* (EPA) carrier protein; 3% to 8% (w/v) sorbitol; 5 to 15 mM methionine; 5 to 20 mM potassium/sodium phosphate buffer at a pH of 6.5 to 7.5; and 0.01% to 0.2% (w/v) surfactant. In preferred embodiments, the concentration of sorbitol is 4% to 6% (w/v). In preferred embodiments, the concentration of methionine is 8 to 12 mM. In preferred embodiments, the concentration of the potassium/sodium phosphate buffer is 8 to 15 mM. Preferably, the composition is a multivalent immunogenic composition comprising an *E. coli* O25B antigen polysaccharide, an *E. coli* O1A antigen polysaccharide, an *E. coli* O2 antigen polysaccharide, and an *E. coli* O6A antigen polysaccharide, wherein each O antigen polysaccharide is independently covalently bound to a exotoxin A of *Pseudomonas aeruginosa* (EPA) carrier protein; 4% to 6% (w/v) sorbitol; 8 to 12 mM methionine; 8 to 15 mM potassium/sodium phosphate buffer at a pH of 6.5 to 7.5; and 0.01% to 0.2% (w/v) surfactant.

Also provided herein are compositions comprising at least one *E. coli* O antigen polysaccharide, wherein the at least one O antigen polysaccharide is covalently bound to a exotoxin A of *Pseudomonas aeruginosa* (EPA) carrier protein; 3% to 12% (w/v) sucrose; 0.1 to 1.5 mM EDTA; 5 to 20 mM potassium/sodium phosphate buffer at a pH of 6.5 to 7.5; and 0.01% to 0.2% (w/v) surfactant. In preferred embodiments, the concentration of sucrose is 3% to 10% (w/v). In preferred embodiments, the concentration of the potassium/sodium phosphate buffer is 8 to 15 mM. Preferably, the composition is a multivalent immunogenic composition comprising an *E. coli* O25B antigen polysaccharide, an *E. coli* O1A antigen polysaccharide, an *E. coli* O2 antigen polysaccharide, and an *E. coli* O6A antigen polysaccharide, wherein each antigen polysaccharide is independently covalently bound to a exotoxin A of *Pseudomonas aeruginosa* (EPA) carrier protein; 3% to 10% (w/v) sucrose; 0.1 to 1.5 mM EDTA; 8 to 15 mM potassium/sodium phosphate buffer at a pH of 6.5 to 7.5; and 0.01% to 0.2% (w/v) surfactant.

In certain embodiments, the *E. coli* O25B, O1A, O2, and O6A antigen polysaccharides are at a weight ratio of 1:1:1:1 or 2:1:1:1.

In certain embodiments, the concentration of sorbitol is 5% (w/v).

In certain embodiments, the concentration of sucrose is 8% (w/v).

In certain embodiments, the concentration of methionine is 10 mM.

In certain embodiments, the concentration of EDTA is 1 mM.

In certain embodiments, the concentration of the potassium/sodium phosphate buffer is 10 mM, and the pH of the potassium/sodium phosphate buffer is 7.0.

In certain embodiments, the concentration of the surfactant is 0.02% (w/v). In preferred embodiments, the surfactant is composed of a hydrophilic head (an OH-group) and a long, hydrophobic tail (carbon-chain, which can comprise at least about 12, 14, 16, 18, 20, 30, 40, 50, 60, 80, 100, 120, 130, or more carbons in the carbon chain). In preferred embodiments, the surfactant is a non-ionic surfactant. In certain embodiments, the surfactant is selected from the group consisting of F-68, PS20, PS40, PS60, and PS80. In certain embodiments, the surfactant is PS80.

In certain embodiments, provided are compositions consisting essentially of an *E. coli* O25B antigen polysaccharide, an *E. coli* O1A antigen polysaccharide, an *E. coli* O2 antigen polysaccharide, and an *E. coli* O6A antigen polysaccharide, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, and an *E. coli* O6A antigen polysaccharide, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80.

In certain embodiments, provided are compositions consisting essentially of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80.

In certain embodiments, provided are compositions consisting essentially of an *E. coli* O25B antigen polysaccharide, an *E. coli* O1A antigen polysaccharide, an *E. coli* O2 antigen polysaccharide, an *E. coli* O6A antigen polysaccharide, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, an *E. coli* O6A antigen polysaccharide, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80.

In certain embodiments, provided are compositions consisting essentially of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80.

Also provided herein are methods of preparing compositions as disclosed herein. In certain embodiments, provided are methods of preparing a composition comprising adding at least one *E. coli* O antigen covalently linked to an EPA carrier, water, salts for a buffer solution (i.e. sodium(di)hydrogen phosphate and potassium(di)hydrogen phosphate [i.e. $Na_2HPO_4$ and $KH_2PO_4$ or $NaH_2PO_4$ and $K_2HPO_4$]), a tonicity modifier (i.e. sorbitol or sucrose), an anti-oxidant (i.e. methionine if the tonicity modifier is sorbitol; EDTA if the tonicity modifier is sucrose), and a surfactant (e.g. PS80) to a container, adjusting the pH to the desired pH (i.e. 6.5 to 7.5, e.g. 7.0), and mixing these components such that a liquid formulation according to the invention is produced. In a preferred embodiment, methods of preparing the composition comprise adding an *E. coli* O25B antigen polysaccharide, an *E. coli* O1A antigen polysaccharide, an *E. coli* O2 antigen polysaccharide, and an *E. coli* O6A antigen polysaccharide, wherein each antigen polysaccharide is covalently bound to a exotoxin A of *Pseudomonas aeruginosa* (EPA) carrier protein; water; potassium phosphate; sodium phosphate; sorbitol; methionine; and PS80 to a container, adjusting the pH to 6.5-7.5 (e.g. 7.0), and mixing each component such that the final concentration of the potassium/sodium phosphate buffer is 5-20 mM (e.g. 10 mM) with a pH of 6.5-7.5 (e.g. 7.0), the final concentration of sorbitol is 3-8% (e.g. 5%) (w/v), the final concentration of methionine is 5-15 mM (e.g. 10 mM), and the final concentration of PS80 is 0.01-0.08% (e.g. 0.02%) (w/v). In another preferred embodiment, methods of preparing the composition comprise adding an *E. coli* O25B antigen polysaccharide, an *E. coli* O1A antigen polysaccharide, an *E. coli* O2 antigen polysaccharide, an *E. coli* O6A antigen polysaccharide, wherein each antigen polysaccharide is covalently bound to a exotoxin A of *Pseudomonas aeruginosa* (EPA) carrier protein; water; potassium phosphate; sodium phosphate; sucrose; EDTA; and PS80 to a container, mixing each component, and adjusting the pH to 6.5-7.5 (e.g. 7.0) such that the final concentration of sucrose is 3-12% (e.g. 8%) (w/v), the final concentration of EDTA is 0.1-1.5 mM (e.g. 1 mM), the final concentration of potassium/sodium phosphate buffer is 5-20 mM (e.g. 10 mM) with a pH of 6.5-7.5 (e.g. 7.0), and the PS80 is 0.01-0.08% (e.g. 0.02%) (w/v).

In certain embodiments, the compositions herein are provided as a liquid composition. By liquid composition, it is meant that the composition is in liquid form at 2-8° C., and preferably stored at 2-8° C.

In certain embodiments, the compositions can be stored and are stable at 2-8° C., at 25° C., or at 40° C. In a preferred embodiment, the composition is stored and is stable at 2-8° C. In certain embodiments, the composition is stable at 2-8° C. for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more months. In certain embodiments, the composition is stable at 25° C. for at least about 1, 2, 3, 4, 5, 6, or more months. In certain embodiments, the composition is stable at 40° C. for at least about 1, 2, 3, 4, 5, 6, 7, 8, 9, 10, 11, 12, or more weeks.

In certain embodiments, the compositions herein are provided as a frozen formulation. By frozen formulation, it is meant that the composition is in a solid form when stored at or below about −18°, e.g. at about −20° C., −40° C., −60° C., −70° C., −80° C. or any temperature in between, or lower. In certain embodiments, the compositions can be stored and are stable at −40° C. or −60° C. depending on the tonicity modifier present in the composition. In certain embodiments, the compositions can be stored and are stable at −70° C. In certain embodiments, the composition comprises sucrose and is stable at −40° C. for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, the composition comprises sorbitol and is stable at −60° C. for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments the composition comprises sorbitol or sucrose and is stable at −70° C. for at least about 1, 2, 3, 4, 5, 6, 7, 8, 9, 10, or more years.

In preferred embodiments, the compositions of the invention do not comprise sodium chloride.

In certain embodiments, the concentration for each O-antigen polysaccharide in the composition is between about 1 and 200 μg/mL, e.g. between about 2 and 100 μg/mL, e.g. between about 4 and 50 μg/mL. In certain embodiments thereof, the polysaccharide:carrier protein ratio is between about 1:10 and about 1:2, e.g between about 1:5 and 1:2 for each O-antigen polysaccharide in the composition.

BRIEF DESCRIPTION OF THE FIGURES

The foregoing summary, as well as the following detailed description of preferred embodiments of the present application, will be better understood when read in conjunction with the appended drawings. It should be understood that the invention is not limited to the precise embodiments shown in the drawings.

In the drawings:

FIG. 1A shows the integration scheme of a size exclusion chromatography-high performance liquid chromatography (SEC-HPLC) chromatogram;

FIG. 1B shows a SEC-HPLC chromatogram demonstrating the results of the experiment before and after freeze/thaw; and FIG. 1C shows a graph plotting the percentage values of the pre-peak 1 upon total peak integration;

DETAILED DESCRIPTION OF THE INVENTION

Figure 1A:
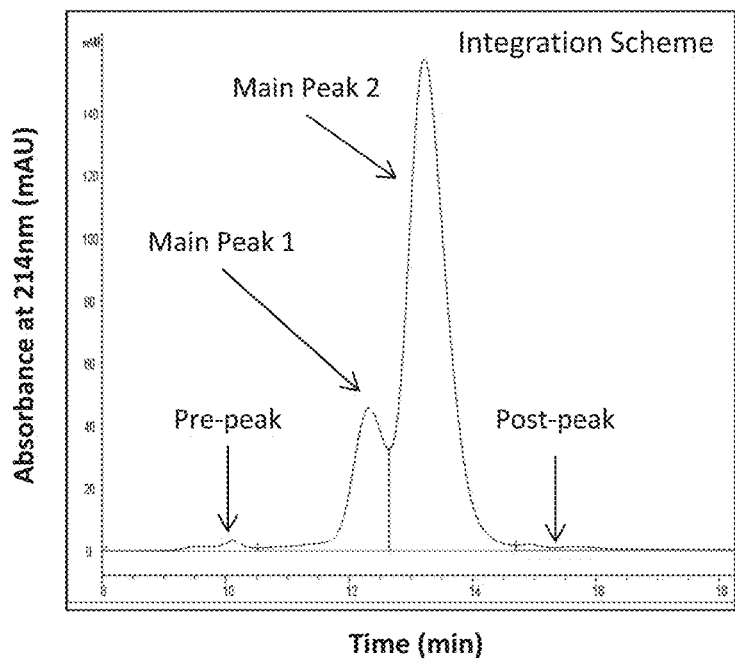
FIGS. 1A, 1B and 1C show that PS20, PS80, and F68, but not sorbitol, were able to prevent freeze/thaw induced aggregation of the ExPEC glycoconjugate under the test conditions: PS20, PS80, F68 and sorbitol were added to an ExPEC glycoconjugate formulation and were subjected to freeze/thaw induced stress.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

As used herein, the terms "O polysaccharide", "O-antigen", "O antigen", "O-antigen polysaccharide", "O-polysaccharide antigen", and the abbreviation "OPS", all refer to the O antigen of Gram-negative bacteria, which is a component of the lipopolysaccharide (LPS) and is specific for each serotype or sero(sub)type of the Gram-negative bacteria. The O antigen usually contains repeating units (RUs) of two to seven sugar residues. As used herein, the RU is set equal to the biological repeat unit (BRU). The BRU describes the RU of an O-antigen as it is synthesized in vivo.

As used herein, the terms "conjugate" and "glycoconjugate" all refer to a conjugation product containing an *E. coli* O antigen covalently bound to a carrier protein (e.g., a exotoxin A of *Pseudomonas aeruginosa* (EPA)). The conjugate can be a bioconjugate, which is a conjugation product prepared in a host cell, wherein the host cell machinery produces the O antigen and the carrier protein and links the O antigen to the carrier protein, e.g., via N-links. The conjugate can also be prepared by other means, for example, by chemical linkage of the protein and sugar antigen.

*E. coli* O antigens in embodiments of the invention include O1A, O2, O6A, and O25B, which are disclosed in WO2015/124769, and WO 2017/035181. Each of these references is herein incorporated by reference in its entirety. Other *E. coli* O antigens can be used as well, e.g. in addition to the specific O1A, O2, O6A and/or O25B antigens, and can for example include, but are not limited to, O antigens from *E. coli* O1, O2, O4, O6, O7, O8, O15, O16, O18, O21, O25, O73, O75 and O153 serotypes or subserotypes thereof.

As used herein, the term "drug substance" refers to the bulk product of an individual glycoconjugate (*E. coli* O antigen polysaccharide covalently coupled to EPA carrier protein, e.g. *E. coli* O25B O antigen covalently coupled to EPA), that is at higher concentration than the product as will be finally administered to a subject. The drug substance can be produced after finalization of the downstream process to purify the glycoconjugate. The drug substance can, for example, be stored in a more concentrated form in a formulation buffer of the invention, for instance in frozen condition, e.g. at minus 70° C.

As used herein, the term "drug product" refers to the formulation of the glycoconjugates, in final form for administration to a subject. The drug product contains all the glycoconjugates (*E. coli* O antigen polysaccharides coupled to EPA carrier protein in case of a multivalent vaccine, e.g. O25B, O1A, O2 and O6A, each individually coupled to an EPA carrier protein, for a four-valent vaccine, and optionally more *E. coli* O antigens coupled to EPA carrier protein if the valency of the vaccine is increased). Drug product can typically be prepared by mixing the drug substances of the respective glycoconjugates, and dilution by formulation buffer if needed, such that the target dose of vaccine is produced. Drug product in a formulation according to the invention can be stored at 2-8° C., and remains stable at that temperature for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 or more months.

The term "about," when used in conjunction with a number, refers to any number within ±1, ±5 or ±10% of the referenced number.

When the O antigen is covalently bound to a protein carrier, the effective amount or dosage for the O antigen is calculated based on only the O antigen polysaccharide moiety in the conjugate.

Diseases associated with ExPEC or ExPEC infections include, but are not limited to, urinary tract infection, surgical-site infection, bacteremia, abdominal or pelvic infection, pneumonia, nosocomial pneumonia, osteomyelitis, cellulitis, pyelonephritis, wound infection, meningitis, neonatal meningitis, peritonitis, cholangitis, soft-tissue infections, pyomyositis, septic arthritis, and sepsis.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to, concomitantly with, or subsequent to the administration of a second therapy (e.g., a composition described herein, or another therapy, e.g., treatment with an antibiotic) to a subject.

As used herein, the term "subject" refers to an animal, preferably a mammal, and may include a non-primate (e.g., a pig, horse, goat, sheep, cat, dog, rabbit, rat, or mouse) and a primate (e.g., a monkey, chimpanzee, or a human). In certain embodiments, a subject is a non-human animal. In another embodiment, a subject is a human. The terms "subject" and "patient" can be used herein interchangeably. The compositions according to the invention are suitable for administration to a subject, and can be used to generate an immune response against ExPEC O-antigens that are encompassed in the composition.

As used herein, an "immunological response" or "immune response" to an antigen or composition refers to the development in a subject of a humoral and/or a cellular immune response to the antigen or an antigen present in the composition.

Compositions Comprising *E. coli* O Antigen Polysaccharides

In one general aspect, the invention relates to a multivalent vaccine containing O-antigen serotypes found predominantly among *E. coli* clinical isolates, which can be used to provide active immunization for the prevention of disease caused by ExPEC having the O-antigen serotypes contained in the vaccine. In one embodiment, the invention relates to a composition comprising at least one *E. coli* O antigen polysaccharide. In certain embodiments, the composition can comprise an *E. coli* O25B antigen polysaccharide. In other embodiments, the composition comprises an *E. coli* O1A, O2, and/or O6A antigen polysaccharide. In preferred embodiments, the composition comprises *E. coli* O1A, O2, O6A and O25B antigen polysaccharides, which are disclosed in WO2015/124769, and WO 2017/035181. Each of these references is herein incorporated by reference in its entirety. In certain embodiments, other or additional *E. coli* O antigen polysaccharide is present in the composition. Such *E. coli* O antigen polysaccharides can include, but are not limited to, O antigens from (sub)serotypes of *E. coli* O1, O2, O4, O6, O7, O8, O15, O16, O18, O21, O25, O73, O75 and O153. Depending on the need, the composition can include more than one additional *E. coli* O antigens, such as 2, 3, 4, 5, 6, 7, 8, 9, 10, 11, 12, 13, 14, 15, 16, 17, 18, 19, 20, or more, additional *E. coli* O antigens, to provide immune protection against multiple *E. coli* serotypes.

In certain embodiments, the compositions and methods can relate to the *E. coli* O25B antigen and one or more additional *E. coli* O antigens. Examples of *E. coli* O antigens can include, but are not limited to *E. coli* O25B, O1A, O2 and O6A antigens.

As used herein an "*E. coli* O25B antigen" refers to an O antigen specific to the *E. coli* O25B serotype. In one embodiment, an *E. coli* O25B antigen comprises the structure of Formula O25B':

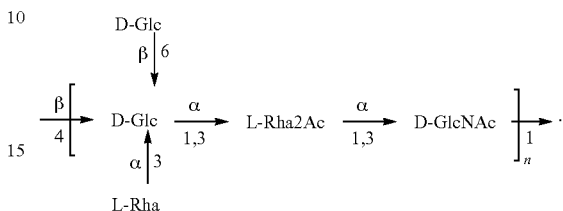

wherein the n in Formula O25B' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment of the invention, the n in Formula O25B' is an integer of 10-20.

As used herein, an "*E. coli* O1A antigen" refers to an O antigen specific to the *E. coli* O1A serotype. In one embodiment, an *E. coli* O1A antigen comprises the structure of Formula O1A':

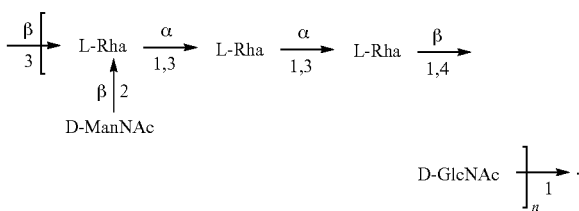

wherein the n in Formula O1A' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n in Formula O1A' is an integer of 7-15.

As used herein, an "*E. coli* O2 antigen" refers to an O antigen specific to the *E. coli* O2 serotype. In one embodiment, an *E. coli* O2 antigen comprises the structure of Formula O2':

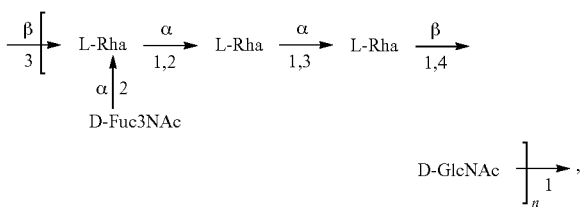

wherein the n in Formula O2' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n in Formula O2' is an integer of 8-16.

As used herein, an "*E. coli* O6 antigen" refers to an O antigen specific to the *E. coli* O6 serotype. In one embodiment, an *E. coli* O6 antigen is an *E. coli* O6A.

As used herein, an "*E. coli* O6A antigen," also referred to as "*E. coli* O6K2 antigen" or "*E. coli* O6Glc antigen," refers to an O antigen specific to the *E. coli* O6A serotype. In one embodiment, an *E. coli* O6A antigen comprises the structure of Formula O6A':

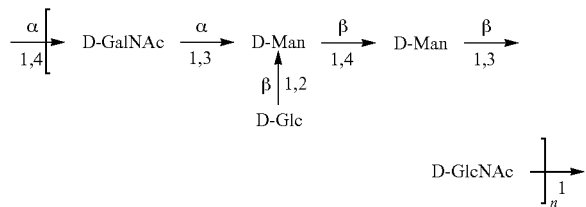

wherein the β 1, 2 linkage is also named (β2 linkage, the n in Formula O6A' is an integer of 1 to 30, 1 to 20, 1 to 15, 1 to 10, 1 to 5, 10 to 30, 15 to 30, 20 to 30, 25 to 30, 5 to 25, 10 to 25, 15 to 25, 20 to 25, 10 to 20, or 15 to 20. In one embodiment, the n in Formula O6A' is an integer of 8-18.

The *E. coli* O antigen polysaccharides in the compositions of the invention are covalently bound (sometimes referred to as "conjugated") to a carrier protein, the carrier protein of the invention being Exotoxin A of *P. aeruginosa*, preferably a detoxified variant thereof (EPA; see, e.g., Ihssen, et al., (2010) Microbial cell factories 9, 61; WO2015/124769). The combination of carrier protein and O antigen polysaccharide is referred to as glycoconjugate. Typically, O antigen from each *E. coli* serotype in the composition is covalently bound to a separate carrier protein, i.e. if the composition comprises four O antigen polysaccharides, each of these is separately and independently coupled to the EPA carrier protein, and the composition thus comprises four different glycoconjugates. One way of making the glycoconjugates is by bioconjugation, wherein the host cell machinery produces the O antigen and the carrier protein and links the O antigen to the carrier protein, e.g., via N-links (see e.g. WO2015/124769 for the preparation of bioconjugates of *E. coli* O antigen O25B, O1A, O2 and O6A polysaccharides to EPA carrier protein). For EPA, various detoxified protein variants have been described in literature and could be used as carrier proteins. A detoxified (or non-toxic) EPA refers to any *Pseudomonas aeruginosa* exotoxin A that lacks ADP ribosylation activity. The ribosylation activity of the wild type EPA is located between about amino acids 400 and 613 of EPA, and for example deleting amino acid Glutamic acid at position 553 from a wild-type EPA, or substituting Histidine at position 426 with Tyrosine in a wild-type EPA, detoxify the EPA molecule. Other amino acids within amino acids 400-613 of wild-type EPA can be modified by, e.g. deletion, addition, or substitution of amino acid residues to eliminate ADP ribosylation activity and therewith toxicity, as known to the skilled person. In preferred embodiments of the invention, the EPA carrier protein is a detoxified variant. In certain non-limiting and exemplary embodiments, the EPA carrier protein can comprise an amino acid sequence as set forth in SEQ ID NO: 1 (being an embodiment of a detoxified EPA), or an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO:1, or has 1, 2, 3, 4, 5, 6, 7, 8, 9, or 10 amino acids difference to SEQ ID NO: 1, any of these optionally further comprising 1, 2, 3, 4, 5, 6, 7, 8, or more recombinantly introduced glycosylation consensus sequences as described below. In specific embodiments, introduction of glycosylation sites is accomplished by insertion of glycosylation consensus sequences (e.g., Asn-X-Ser (Thr), wherein X can be any amino acid except Pro; or preferably Asp(Glu)-X-Asn-Z-Ser(Thr), wherein X and Z are independently selected from any natural amino acid except Pro (SEQ ID NO: 2) (see, e.g., WO 2006/119987 and WO2015/124769)) anywhere in the primary structure of the EPA protein. In preferred embodiments, the EPA carrier protein comprises one or more recombinantly introduced N-linked glycosylation consensus sites having amino acid sequence Asp(Glu)-X-Asn-Z-Ser(Thr), wherein X and Z are independently selected from any natural amino acid except Pro (SEQ ID NO: 2). In certain embodiments, the EPA carrier protein comprises one, two, three, four, five, six, seven, eight, or more of such introduced consensus sequences. In other embodiments, the EPA does not comprise such introduced N-linked glycosylation consensus sites, for instance when the glycoconjugate is prepared using classical conjugation chemistry (see e.g., U.S. Pat. No. 5,370,872; Cryz et al, 1990, Infection and Immunity 58: 373-377).

In certain embodiments, the *E. coli* O-antigens are covalently bound to the carrier protein at a polysaccharide-to-protein weight/weight ratio of about 1:20 to 20:1, preferably 1:10 to 10:1, e.g. 1:10 to 3:1. In certain non-limiting embodiments for bioconjugates, the ratio of polysaccharide/protein is between about 0.1 and 0.5 (i.e. polysaccharide:protein is about 1:10 to 1:2, e.g. about 1:2, 1:3, 1:4, 1:5, 1:6, 1:7, 1:8, 1:9, 1:10, or any value in between) for each bioconjugate, depending on the O-antigen serotype.

In certain non-limiting embodiments, the *E. coli* O antigen polysaccharides can be present in the composition at a concentration of about 1 to 200 µg/mL for each O antigen polysaccharide, e.g., about 2 to 100 µg/mL, e.g. about 4 to 50 µg/mL, e.g. about 4 to 48 µg/mL, e.g. about 8 to 48 µg/mL, e.g. about 4 to 32 µg/mL, e.g. about 8 to 32 µg/mL, e.g., 8, 16, 20, or 32 µg/mL or any value in between. Preferably, in a composition of at least two *E. coli* O antigen polysaccharides, each O antigen polysaccharide is present in weight ratios of between 1:1 to 1:2, or any value in between, for each combination of O antigen polysaccharides in the composition.

In certain non-limiting embodiments the O-antigen polysaccharides are present in the composition at a concentration of total O-antigen polysaccharides of about 4 to 1000 µg/mL, e.g. about 10 to 500 µg/mL, e.g. about 20 to 250 µg/mL, e.g. about 24 to 120 µg/mL.

In certain non-limiting embodiments, the total concentration for the EPA carrier protein in the composition can for instance be between about 40 and 2000 µg/mL, e.g. about 100 to 1500 µg/mL, e.g. about 200 to 1200 µg/mL, e.g. about 250 to 600 µg/mL.

In certain embodiments, the composition comprises O25B, O1A, O2 and O6A antigen polysaccharides at a weight ratio of 1:1:1:1, wherein each of the O antigen polysaccharides is covalently bound to an EPA carrier protein. In another embodiment, the composition comprises the *E. coli* O25B, O1A, O2 and O6A antigen polysaccharides at a weight ratio of 2:1:1:1, wherein each of the O antigen polysaccharides is covalently bound to an EPA carrier protein. In each of such embodiments, the O25B antigen polysaccharide can, as a non-limiting example, be present at a concentration of about 8, 16, or 32 µg/mL.

The compositions described herein are useful in the treatment and prevention of infection of subjects (e.g., human subjects) with ExPEC. In certain embodiments, in addition to comprising *E. coli* O antigen polysaccharides covalently bound to an EPA carrier protein, the compositions described herein comprise a pharmaceutically acceptable carrier. As used herein, the term "pharmaceutically acceptable" means approved by a regulatory agency of a Federal or a state government or listed in the U.S. Pharmacopeia or other generally recognized pharmacopeia for use in animals, and more particularly in humans. The term "carrier," as used herein in the context of a pharmaceutically acceptable carrier, refers to a diluent, adjuvant, excipient, or vehicle with which the pharmaceutical composition is administered. Water in the compositions of the invention is preferably water for injection.

The compositions provided herein comprise a surfactant. Surfactants as used herein are organic compounds that are amphiphilic, meaning they contain both hydrophobic groups (their tails) and hydrophilic groups (their heads). In preferred embodiments, the surfactant is composed of a hydrophilic head (comprising an OH-group) and a long hydrophobic tail (carbon-chain, which can comprise at least about 12, 14, 16, 18, 20, 30, 40, 50, 60, 80, 100, 120, 130, or more carbons in the carbon chain). Preferred surfactants according to the invention are non-ionic surfactants. Examples of surfactants suitable for compositions of the invention include, but are not limited to, polysorbate 20 (PS20), polysorbate 40 (PS40), polysorbate 60 (PS60), polysorbate 80 (PS80), and Pluronic® F-68 (F-68). In a preferred embodiment, the surfactant is PS80. In certain embodiments, the surfactant in the composition is provided at a concentration of 0.01% (weight/volume (w/v)) to 0.2% (w/v). In certain embodiments, the surfactant in the composition is provided at a concentration of 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, or any value in between. For embodiments where F-68 is the surfactant, the concentration is preferably from about 0.05% to about 0.2%. For embodiments where PS20, PS40, PS60, or PS80 is the surfactant, the concentration is preferably from about 0.01% to about 0.08%, e.g. about 0.01%, 0.02%, 0.03%, 0.04%, 0.05%, 0.06%, 0.07%, 0.08%, or any value in between.

The compositions provided herein further comprise a buffer with a specific pH. According to the present invention, the composition comprises a potassium/sodium phosphate buffer. Concentration ranges for such buffer can, for example, be about 5 mM to about 20 mM, about 8 mM to about 15 mM, about 8 mM to about 13 mM, about 9 mM to about 11 mM. In certain embodiments, the buffer is provided at a concentration of 8 mM, 9 mM, 10 mM, 11 mM, 12 mM, 13 mM, 14 mM, 15 mM, or any value in between. In certain embodiments, the buffer concentration is from about 8 mM to about 15 mM. In a preferred embodiment, the composition comprises the buffer at a concentration of 10 mM. pH ranges for such buffers can, for example, be about pH 6.5 to about pH 7.5, about pH 6.6 to about pH 7.4, about pH 6.7 to about pH 7.3, about pH 6.8 to about pH 7.2, about pH 6.9 to about pH 7.1. In certain embodiments, the pH can be 6.5, 6.6, 6.7, 6.8, 6.9, 7.0, 7.1, 7.2, 7.3, 7.4, 7.5, or any value in between. In a preferred embodiment the pH of the buffer is 7.0. In a preferred embodiment, the composition comprises a potassium/sodium phosphate buffer at a concentration of 10 mM and at a pH of 7.0.

Potassium/sodium phosphate buffer solutions can, for example, comprise potassium from $K_2HPO_4$ (dibasic) or $KH_2PO_4$ (monobasic) and sodium from $Na_2HPO_4$ (dibasic) or $NaH_2PO_4$ (monobasic). In certain embodiments, the potassium/sodium phosphate buffer comprises a monobasic potassium phosphate ($KH_2PO_4$) and a dibasic sodium phosphate ($Na_2HPO_4$). In certain embodiments, the potassium/sodium phosphate buffer comprises a dibasic potassium phosphate ($K_2HPO_4$) and a monobasic sodium phosphate ($NaH_2PO_4$). The molar ratio between the monobasic phosphate species and the dibasic phosphate species ($[H_2PO_4]^-/[HPO_4]^{2-}$), regardless of the counter ion, ranges between 5.13 and 0.52.

The compositions provided herein can further comprise a tonicity modifier (sometimes also referred to as 'stabilizer'). The tonicity modifiers used in the composition of the invention are either sucrose or sorbitol, depending on the other excipients, as defined herein. In certain embodiments, the composition comprises sucrose. In certain embodiments, the composition comprises sucrose at a concentration range of about 3% to about 12% (w/v), about 3% to about 11% (w/v), about 3% to about 10% (w/v), about 4% to about 10% (w/v), about 5% to about 9% (w/v), about 6% to about 9% (w/v). In certain embodiments, the sucrose is provided at a concentration of 3%, 4%, 5%, 6%, 7%, 8%, 9%, 10%, 11%, 12%, or any value in between. In a preferred embodiment, the composition comprises sucrose at a concentration of about 3% to about 10%. In a preferred embodiment, the composition comprises sucrose at a concentration of 8%. In other preferred embodiments, the composition comprises sorbitol. In a preferred embodiment, the composition comprises sorbitol at a concentration of about 3% to about 8% (w/v), about 3% to about 7% (w/v), about 4% to about 6% (w/v). In preferred embodiments, the composition comprises sorbitol at a concentration of about 4% to about 6% (w/v). In certain embodiments, the composition comprises sorbitol at a concentration of about 3%, 4%, 5%, 6%, 7%, 8%, or any value in between. In a preferred embodiment, the composition comprises sorbitol at a concentration of 5%.

The compositions provided herein further comprise an anti-oxidant. The anti-oxidant used in the compositions of the present invention is EDTA or methionine, depending on the other excipients, as described herein. In certain embodiments, the composition comprises EDTA. In certain embodiments, the composition comprises EDTA at a concentration of about 0.1 mM to about 1.5 mM, about 0.2 mM to about 1.4 mM, about 0.5 mM to about 1.3 mM, about 0.7 mM to about 1.2 mM, about 0.8 mM to about 1.2 mM, about 0.9 mM to about 1.1 mM. In certain embodiments, the EDTA is provided at a concentration of 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, or any value in between. In a preferred embodiment, the composition comprises EDTA at a concentration of 1.0 mM. The compositions of the invention that comprise EDTA also comprise sucrose. In other embodiments, the composition comprises methionine. In certain embodiments, the composition comprises methionine at a concentration of about 5 mM to about 15 mM, about 6 mM to about 14 mM, about 7 mM to about 13 mM, about 8 mM to about 12 mM, about 9 mM to about 11 mM. In a preferred embodiment, the composition comprises methionine at a concentration of about 8 mM to about 12 mM. In certain embodiments, the methionine is provided at a concentration of 5 mM, 6 mM, 7 mM, 8 mM, 9 mM, 10 mM, 11 mM, 12 mM, 13 mM, 14 mM, 15 mM, or any value in between. In a preferred embodiment, the composition comprises methionine at a concentration of 10 mM. The compositions of the invention that comprise methionine also comprise sorbitol.

Provided are compositions comprising an *E. coli* O25B antigen polysaccharide, an *E. coli* O1A antigen polysaccharide, an *E. coli* O2 antigen polysaccharide, and an *E. coli* O6A antigen polysaccharide, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions consisting essentially of an *E. coli* O25B antigen polysaccharide, an *E. coli* O1A antigen polysaccharide, an *E. coli* O2 antigen polysaccharide, and an *E. coli* O6A antigen polysaccharide, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, and an *E. coli* O6A antigen polysaccharide, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions comprising an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions consisting essentially of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 5% (w/v) sorbitol; 10 mM methionine; 10 mM potassium/sodium phosphate buffer at a pH of 7.0; and 0.02% PS80.

Provided are compositions comprising an *E. coli* O25B antigen polysaccharide, an *E. coli* O1A antigen polysaccharide, an *E. coli* O2 antigen polysaccharide, an *E. coli* O6A antigen polysaccharide, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also, provided are compositions consisting essentially of an *E. coli* O25B antigen polysaccharide, an *E. coli* O1A antigen polysaccharide, an *E. coli* O2 antigen polysaccharide, an *E. coli* O6A antigen polysaccharide, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, an *E. coli* O6A antigen polysaccharide, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also provided are compositions comprising an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also provided are compositions consisting essentially of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80. Also provided are compositions consisting of an *E. coli* O25B antigen polysaccharide, an *E. coli* O1A antigen polysaccharide, an *E. coli* O2 antigen polysaccharide, an *E. coli* O6A antigen polysaccharide, and 1, 2, 3, 4, 5, 6, 7, 8, 9, 10, 11, 12, 13, 14, 15, 16, 17, 18, 19, or 20 other *E. coli* O antigen polysaccharides, wherein each O antigen polysaccharide is covalently bound to a exotoxin A of *Pseudomonas aeruginosa* (EPA) carrier protein; 8% (w/v) sucrose; 1 mM EDTA; 10 mM potassium/sodium phosphate buffer at a pH of 7.0; and 0.02% PS80.

The compositions described herein can optionally additionally comprise a preservative, such as the mercury derivative thimerosal, phenoxyethanol, or parabens. In a specific embodiment, the pharmaceutical compositions described herein comprise 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein can be administered before, concomitantly with, or after administration of said composition. In some embodiments, the term "adjuvant" refers to a compound that when administered in conjunction with or as part of a composition described herein augments, enhances and/or boosts the immune response to a bioconjugate, but when the adjuvant compound is administered alone does not generate an immune response to the bioconjugate. Adjuvants can enhance an immune response by several mechanisms including, e.g., lymphocyte recruitment, stimulation of B and/or T cells, and stimulation of macrophages. In certain embodiments, the compositions described herein do not comprise an adjuvant besides the bioconjugates and excipients, and/or are not administered in combination with an adjuvant besides the bioconjugates and the excipients (in case the bioconjugates or excipients would comprise some intrinsic adjuvant properties, these would be disregarded and no additional extrinsic adjuvant would be added in these embodiments).

Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS03 (GlaxoSmithKline), AS04 (GlaxoSmithKline), imidazopyridine compounds (see WO2007/109812), imidazoquinoxaline compounds (see WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057,540). Other adjuvants are oil in water emulsions (such as squalene or peanut oil), optionally in combination with immune stimulants, such as monophosphoryl lipid A (see Stoute et al., 1997, N. Engl. J. Med. 336, 86-91). Another adjuvant is CpG (Bioworld Today, Nov. 15, 1998).

In certain embodiments, the compositions described herein are formulated to be suitable for the intended route of administration to a subject. For example, the compositions described herein can for instance be formulated to be suitable for intramuscular, subcutaneous, parenteral, oral, intranasal, intradermal, transdermal, colorectal, intraperitoneal, intratracheal, topical, rectal or pulmonary administration. In certain embodiments, the compositions described herein are useful for administration by intramuscular injection. In other embodiments, the compositions described herein can be administered intradermally. In other embodiments, the compositions described herein can be delivered via the skin.

In another aspect, also provided herein are drug substance compositions comprising at least one of the four conjugates described in detail herein (i.e. representing O-antigen from E. coli serotypes O25B, O1A, O2, or O6A), in the formulations described herein. Such compositions that comprise only one or a subset of the four conjugates can for instance be useful for storage of bulk antigens, e.g. as drug substance before compounding into the final drug product, and share useful stability characteristics described for the drug product compositions comprising all of the four conjugates.

Methods/Uses

The compositions of the invention can, for instance, be used for a method of inducing an immune response to ExPEC in a subject in need thereof. Preferably, the immune response is effective to prevent or treat a disease associated with ExPEC in the subject in need thereof. The method comprises administering to the subject a composition according to the invention.

In certain embodiments, compositions provided herein can be stored in a container. Suitable containers can include, but are not limited to, bags, vials, syringes, bottles, and test tubes. In certain embodiments, a vial with a stopper capable of being pierced by a syringe comprises any of the compositions described herein. The containers provided herein can be formed from a variety of materials such as glass (e.g., borosilicate glass), metal, or plastic (e.g., polycarbonates). In certain embodiments, the container is for instance a vial of type I borosilicate glass. In other embodiments, the container is a glass syringe with either luer lock or staked needle. In other embodiments, the container is a vial or syringe of plastic material, such as polycarbonate (PC) or polyethylene terephthalate glycol (PETG), which material for instance was shown to be compatible with drug substance according to the invention. Vials may optionally contain a rubber stopper, for instance from (chloro/bromo) butyl rubber coated with a fluoropolymer film (e.g. Flurotec [ethylene tetrafluoroethylene (EFTE)] or Teflon [fluorinated ethylene propylene (FEP)]). Other materials and container types can also be used, and compatibility with the formulations of the invention can be determined by those skilled in the art based upon the present disclosure.

In certain embodiments, drug substance is stored in polycarbonate containers, e.g. bottles. In certain embodiments, drug substance is stored in polyethylene terephthalate glycol containers, e.g. bottles. In certain embodiments, drug product is stored in glass containers, e.g. vials.

The formulations provided herein improve the stability of the glycoconjugates in the compositions. By stable, it is generally meant that the composition retains its physical stability and/or chemical stability and/or biological activity upon storage. Preferably, the composition essentially retains its physical and chemical stability and its biological activity upon storage. Physical stability, chemical stability, and biological activity can be determined by those of skill in the art utilizing methods disclosed herein and methods known in the art. For the present invention, a composition is considered 'stable' (and the corresponding formulation is considered 'stabilizing'), if there is 5% or less change in the size-exclusion chromatography HPLC pre-peak (indicative of aggregation of the glycoconjugate) as compared to time point zero, as described in the examples herein. For example, the existing ExPEC vaccine composition (in 25 mM Tris pH 7.4, 2.7 mM KCl, 137 mM NaCl) shows a more than 5% increase of the pre-peak at 8 weeks at 40° C., and is thus not stable at 8 weeks at this temperature, whereas the compositions of the invention show less than 5% increase of the pre-peak after 12 weeks at 40° C. and are thus stable for at least 12 weeks at this temperature. The compositions of the invention are stable in a glass container at 2-8° C. for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more, months. The compositions of the invention are also stable in plastic containers for at least 7 days at 25° C., which allows processing of the ExPEC glycoconjugate product under these conditions.

In certain embodiments, the compositions herein are provided as a liquid composition. By liquid composition, it is meant that the composition is in liquid form when at 2-8° C., and preferably stored at 2-8° C. Optionally, the liquid composition is stored at 25° C. or at 40° C., for instance for accelerated stability testing under thermal stress conditions.

In certain embodiments, the compositions can be stored and are stable at 2-8° C., at 25° C., or at 40° C. In a preferred embodiment, the composition is stored and is stable at 2-8° C. In certain embodiments, the composition is stable at 2-8° C. for at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or more, months. In certain embodiments, the composition is stable at 25° C. for 1, 2, 3, 4, 5, 6, or more months. In certain embodiments, the composition is stable at 40° C. for at least about 1, 2, 3, 4, 5, 6, 7, 8, 9, 10, 11, 12, or more weeks.

In certain embodiments, the compositions herein are provided as a frozen composition. By frozen composition, it is meant that the composition is in a solid form when stored at or below about −18°, e.g. at about −20° C., −40° C., −60° C., −70° C., −80° C. or any temperature in between, or lower. In certain embodiments, the compositions can be stored and are stable at −40° C. or −60° C. depending on the tonicity modifier present in the composition. In certain embodiments, the compositions can be stored and are stable at −70° C. In certain embodiments, the composition comprises sucrose and is stable at −40° C. for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments, the composition comprises sorbitol and is stable at −60° C. for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or more months. In certain embodiments the composition comprises sorbitol or sucrose and is stable at −70° C. for at least about 1, 2, 3, 4, 5, 6, 7, 8, 9, 10, or more years. The compositions of the present invention are designed to be more stable than the old composition formulation described previously. Stability of the composition can be determined by methods described herein and methods known in the art. Utilizing these methods, the compositions of the present invention will be more stable over a given time period at a given temperature as compared to compositions of the old formulation over the same time period and same temperature.

Also provided herein are methods of preparing compositions as disclosed herein. In certain embodiments, provided are methods of preparing a composition comprising adding at least one E. coli O antigen covalently linked to an EPA carrier, water, salts for a buffer solution (i.e. sodium(di)hydrogen phosphate and potassium(di)hydrogen phosphate [i.e. $Na_2HPO_4$ and $KH_2PO_4$ or $NaH_2PO_4$ and $K_2HPO_4$]), a tonicity modifier (i.e. sorbitol or sucrose), an anti-oxidant (i.e. methionine if tonicity modifier is sorbitol, EDTA if tonicity modifier is sucrose), and a surfactant (e.g. PS80) to a container, adjusting the pH to the desired pH (i.e. 6.5 to 7.5, e.g. 7.0), and mixing these components such that a liquid formulation according to the invention is produced. In a preferred embodiment, methods of preparing the composition comprise adding an E. coli O25B antigen polysaccharide, an E. coli O1A antigen polysaccharide, an E. coli O2 antigen polysaccharide, and an E. coli O6A antigen polysaccharide, wherein each antigen polysaccharide is covalently bound to a exotoxin A of Pseudomonas aeruginosa (EPA) carrier protein; water; potassium phosphate; sodium phosphate; sorbitol; methionine; and PS80 to a container, adjusting the pH to 7.0, and mixing each component such that the final concentration of the potassium/sodium phosphate buffer is 10 mM with a pH of 7.0, sorbitol is 5% (w/v), methionine is 10 mM, and PS80 is 0.02% (w/v). One, non-limiting and exemplary, way of preparing a formulation according to the invention is as follows: to about 3.5 liter of water is added: 3.3696 g $KH_2PO_4$ (Mw=136.09 g/mol), 2.1635 g $Na_2HPO_4$ (Mw=141.96 g/mol), 200 g sorbitol, 5.9684 g Methionine (Mw=149.21 g/mol), 8 mL of 10% (w/v) PS80 stock, which results in a pH of about 6.73, which is subsequently adjusted with about 500 μL of 10 N NaOH to target pH=7.0, and the volume is adjusted to 4 liter with water. A formulation comprising sucrose and EDTA instead of sorbitol and methionine can be prepared in an analogous manner, which is clear to the skilled person having common general knowledge and the information provided herein. One possible way to prepare a composition according to the invention is by buffer exchange, e.g. using tangential flow filtration, filtration, dialysis, size exclusion chromatography, or the like, to exchange the formulation that is prepared as described above for any buffer in which the ExPEC glycoconjugate is present, for instance during or after a purification step of the ExPEC glycoconjugate. Such a buffer exchange step is routine for a skilled person, using the information provided herein.

The following examples of the invention are to further illustrate the nature of the invention. It should be understood that the following examples do not limit the invention and that the scope of the invention is to be determined by the appended claims.

EMBODIMENTS

Embodiment 1 is an immunogenic composition comprising one or more of an E. coli O25B antigen polysaccharide, an E. coli O1A antigen polysaccharide, an E. coli O2 antigen polysaccharide, and an E. coli O6A antigen polysaccharide, preferably all four of the E. coli O25B, O1A, O2 and O6A antigen polysaccharides, wherein each antigen polysaccharide is covalently bound to a exotoxin A of Pseudomonas aeruginosa (EPA) carrier protein; 3% to 8% (preferably 4% to 6%) (w/v) sorbitol; 5 to 15 mM (preferably 8 to 12 mM) methionine; 5 to 20 mM (preferably 8 to 15 mM) potassium/sodium phosphate buffer at a pH of 6.5 to 7.5; and 0.01% to 0.2% (w/v) surfactant.

Embodiment 2 is the immunogenic composition of embodiment 1, wherein the E. coli O25B, O1A, O2, and O6A antigen polysaccharides are at a weight ratio of 1:1:1:1 or 2:1:1:1.

Embodiment 3 is the immunogenic composition of embodiment 1 or 2, wherein the concentration of sorbitol is 5% (w/v).

Embodiment 4 is the immunogenic composition of any of embodiments 1-3, wherein the concentration of methionine is 10 mM.

Embodiment 5 is the immunogenic composition of any of embodiments 1-4, wherein the concentration of the potassium/sodium phosphate buffer is 10 mM, and the pH of the potassium/sodium phosphate buffer is 7.0.

Embodiment 6 is the immunogenic composition of any of embodiments 1-5, wherein the surfactant comprises a hydrophilic head and a hydrophobic tail, preferably, wherein the surfactant is selected from the group consisting of F-68, PS20, and PS80.

Embodiment 7 is the immunogenic composition of embodiment 6, wherein the surfactant is PS80.

Embodiment 8 is the immunogenic composition of embodiment 7, wherein the concentration of the surfactant is 0.02% (w/v).

Embodiment 9 is an immunogenic composition comprising:
  a. an E. coli O25B antigen polysaccharide, an E. coli O1A antigen polysaccharide, an E. coli O2 antigen polysaccharide, and an E. coli O6A antigen polysaccharide, wherein each antigen polysaccharide is covalently bound to a exotoxin A of Pseudomonas aeruginosa (EPA) carrier protein;
  b. 5% (w/v) sorbitol;
  c. 10 mM methionine;
  d. 6.19 mM $KH_2PO_4$ and 3.81 mM $Na_2HPO_4$ buffer at a pH of 7.0; and
  e. 0.02% (w/v) PS80.

Embodiment 10 is an immunogenic composition comprising one or more of an E. coli O25B antigen polysaccharide, an E. coli O1A antigen polysaccharide, an E. coli O2 antigen polysaccharide, and an E. coli O6A antigen polysaccharide, preferably all four of the E. coli O25B, O1A, O2 and O6A antigen polysaccharides, wherein each antigen polysaccharide is covalently bound to a exotoxin A of Pseudomonas aeruginosa (EPA) carrier protein; 3% to 12% (preferably 3 to 10%) (w/v) sucrose; 0.1 to 1.5 mM EDTA; 5 to 20 mM (preferably 8 to 15 mM) potassium/sodium phosphate buffer at a pH of 6.5 to 7.5; and 0.01% to 0.2% (w/v) surfactant.

Embodiment 11 is the immunogenic composition of embodiment 10, wherein the E. coli O25B, O1A, O2, and O6A antigen polysaccharides are at a weight ratio of 1:1:1:1 or 2:1:1:1.

Embodiment 12 is the immunogenic composition of embodiment 10 or 11, wherein the concentration of sucrose is 8% (w/v).

Embodiment 13 is the immunogenic composition of any of embodiments 10-12, wherein the concentration of EDTA is 1 mM.

Embodiment 14 is the immunogenic composition of any of embodiments 10-13, wherein the concentration of the potassium/sodium phosphate buffer is 10 mM, and the pH of the potassium/sodium phosphate buffer is 7.0.

Embodiment 15 is the immunogenic composition of any of embodiments 10-14, wherein the surfactant comprises a hydrophilic head and a hydrophobic tail, preferably wherein the surfactant is selected from the group consisting of F-68, PS20, and PS80.

Embodiment 16 is the immunogenic composition of embodiment 15, wherein the surfactant is PS80.

Embodiment 17 is the immunogenic composition of embodiment 16, wherein the concentration of the surfactant is 0.02% (w/v).

Embodiment 18 is an immunogenic composition comprising:
  a. an *E. coli* O25B antigen polysaccharide, an *E. coli* O1A antigen polysaccharide, an *E. coli* O2 antigen polysaccharide, an *E. coli* O6A antigen polysaccharide, wherein each antigen polysaccharide is covalently bound to a exotoxin A of *Pseudomonas aeruginosa* (EPA) carrier protein;
  b. 8% (w/v) sucrose;
  c. 1 mM EDTA;
  d. 10 mM potassium/sodium phosphate (e.g. 6.19 mM $KH_2PO_4$ and 3.81 mM $Na_2HPO_4$) buffer at a pH of 7.0; and
  e. 0.02% (w/v) PS80.

Embodiment 19 is the immunogenic composition of any one of embodiments 1-18, wherein the concentration for each O-antigen polysaccharide is between about 1 and 200 µg/mL, preferably between 1 and 100 µg/mL, more preferably between 2 and 50 µg/mL, e.g. between about 4 µg/mL and 32 µg/mL.

Embodiment 20 is the immunogenic composition of any one of embodiments 1-19, wherein the polysaccharide: carrier protein (weight:weight) ratio is between about 1:10 and about 1:2, e.g. between about 1:5 and about 1:2 for each O-antigen polysaccharide.

Embodiment 21 is the immunogenic composition of any one of embodiments 1-20 in a liquid form suitable for administration by injection or infusion.

Embodiment 22 is the immunogenic composition of any one of embodiments 1-21 for inducing an immune response in a subject in need thereof.

Embodiment 23 is use of the immunogenic composition of any one of embodiments 1-21 for the manufacture of a medicament for inducing an immune response in a subject in need thereof.

Embodiment 24 is a composition according to any one of embodiments 1-21 in a glass container.

Embodiment 25 is a composition according to any one of embodiments 1-21 in a polycarbonate container.

Embodiment 26 is a composition according to anyone of embodiments 1-21 in a polyethylene terephthalate glycol container.

Embodiment 27 is a composition according to any one of embodiments 1-21 in a vial.

Embodiment 28 is a composition according to any one of embodiments 1-21 in a syringe.

Embodiment 29 is a composition according to any one of embodiments 1-21 or 24-28, which is stable for at least 6 months, preferably at least 12 months, more preferably at least 18 months, more preferably at least 24 months, more preferably at least 25, 26, 27, 28, 29, 30, 31, 32, 33, 34, 35, 36, or more, months, when stored at a temperature of 2-8° C.

Embodiment 30 is a method to stably maintain a liquid immunogenic composition comprising an *E. coli* O antigen covalently coupled to an EPA carrier protein, comprising storing a composition according to any one of embodiments 1-21 or 24-29 at a temperature of 2-8° C. for at least 6 months, preferably at least 12 months, more preferably at least 18 months, more preferably at least 24 months, more preferably at least 25, 26, 27, 28, 29, 30, 31, 32, 33, 34, 35, 36, or more, months.

EXAMPLES

Example 1: Addition of Surfactant Prevents Freeze/Thaw Induced Aggregation of ExPEC Glycoconjugate To determine which combination of excipients could be added to the *E. coli* O25B, O1A, O2, O6A antigen polysaccharides each independently covalently bound to a separate (i.e. total four separate glycoconjugates) exotoxin A of *Pseudomonas aeruginosa* (EPA), hereinafter referred to as the ExPEC glycoconjugate, to aid with stabilization upon freeze/thaw, agitation, thermal induced stress, and metal-induced oxidation stress, different excipients were added to an initial ExPEC glycoconjugate formulation (ExPEC glycoconjugate, 25 mM Tris, pH 7.4, 137 mM NaCl, 2.7 mM KCl) (hereinafter referred to as the "Old" formulation, which is the formulation currently used in a phase 2 clinical trial for the ExPEC glycoconjugate, ClinicalTrials.gov Identifier: NCT02546960), and the resulting formulation was tested for increased stabilization by the appropriate methods.

In the old formulation (sometimes also referred to as "control" herein), the ExPEC glycoconjugate aggregated upon being subjected to freeze/thaw induced stress. Aggregation of the ExPEC glycoconjugate is visible as a pre-peak in a size exclusion chromatography-high performance liquid chromatography (SEC-HPLC) profile (see, e.g., FIGS. 1A and 1B), in which the pre-peak 1 is an indicator for instability upon being subjected to a stress.

Figure 1B:
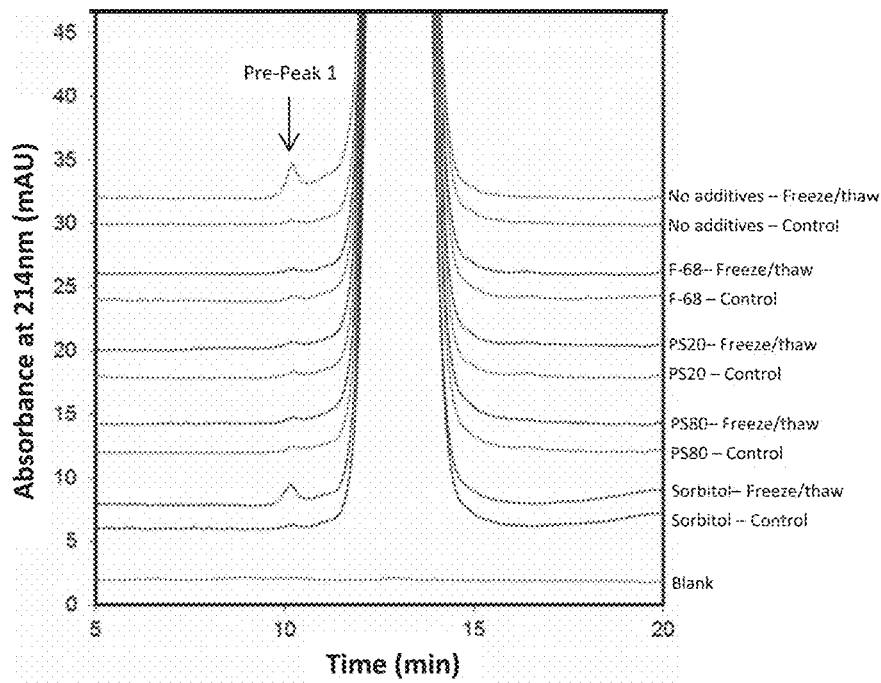

Initially, a cryoprotectant (e.g., sorbitol) was added to the ExPEC glycoconjugate formulation and the subsequent formulation was tested to determine if the stability was increased upon being subjected to freeze/thaw induced stress. It was found that the addition of sorbitol did not protect the ExPEC glycoconjugate from freeze/thaw induced aggregation as measured by SEC-HPLC (FIG. 1B).

Figure 1C:
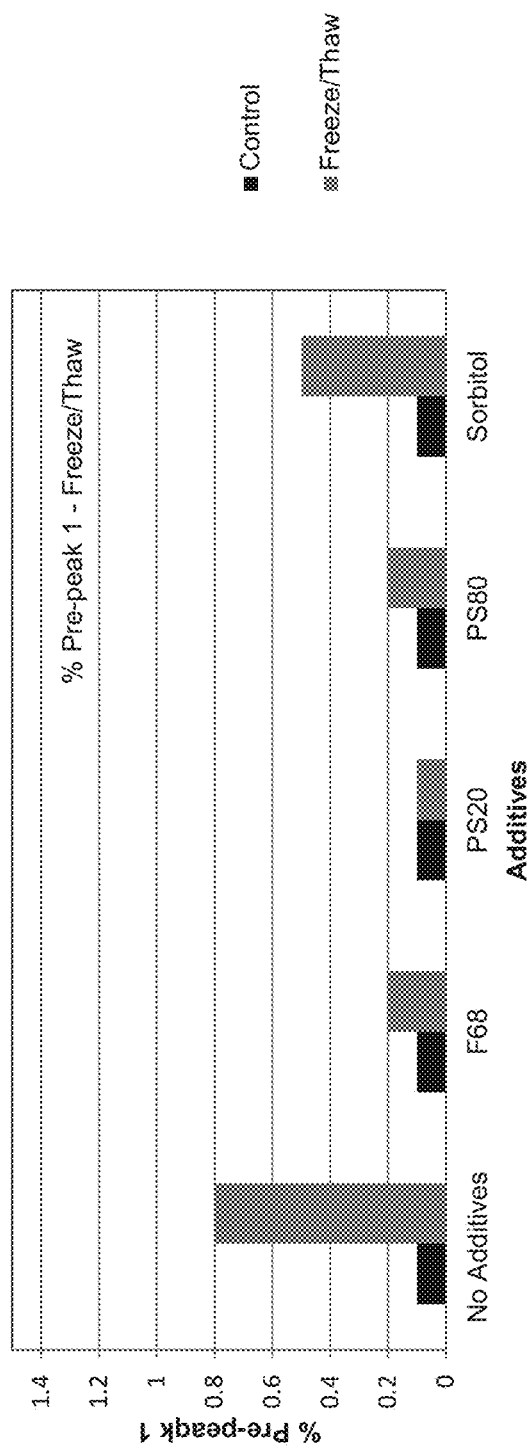

Surprisingly however, addition of a surfactant (e.g., F-68 [also known as poloxamer 188, or Pluronic F-68], PS20, or PS80) to the ExPEC glycoconjugate formulation increased the stability of the ExPEC glycoconjugate when subjected to freeze/thaw induced stress. Specifically, the surfactant prevented aggregation of the ExPEC glycoconjugate when exposed to a freeze/thaw induced stress. Addition of 0.01% PS-80, 0.01% PS 20, or 0.1% F-68 (all w/v) to the ExPEC glycoconjugate prevented freeze/thaw induced aggregation as measured by SEC-HPLC (FIG. 1B and FIG. 1C). Each tested surfactant (all non-ionic surfactants) was composed of a hydrophilic head (comprising an OH-group) and a long hydrophobic tail (carbon-chain, which can comprise at least about 12, 14, 16, 18, 20, 30, 40, 50, 60, 80, 100, 120, 130, or more carbons in the carbon chain). While not wishing to be bound by the theory, it is believed that these physical properties allowed the surfactants tested to prevent freeze/thaw induced aggregation of the ExPEC glycoconjugate. In further development, PS80 was used as the excipient to prevent freeze/thaw induced aggregation, as this particular surfactant has additional advantages related to easy implementation for late stage development of the ExPEC glycoconjugate.

Example 2: Formulation Evaluation for Buffer, pH Value, and Tonicity Modifier After demonstrating that surfactants are capable of preventing freeze/thaw induced aggregation of the ExPEC glycoconjugate, a suitable buffer, pH, and a tonicity modifier for the formulation was investigated. In a follow-up experiment, several formulations were investigated, covering different buffer-pH combinations, in the presence of NaCl (150 mM) or 5% sorbitol (w/v) as a tonicity modifier, and all containing PS80 (0.01% (w/v). Old formulation (25 mM Tris, pH 7.4, 137 mM NaCl, 2.7 mM KCl) was used as a control. Multiple concentrations of the ExPEC glycoconjugate (e.g. 16 or 8 µg/mL for each polysaccharide) were tested, but we did not observe an effect of concentration differences in stabilization of the formulations tested (data not shown).

Several stresses were applied to these formulations including freeze/thaw, agitation, light exposure, and thermal stress at various temperatures (e.g., 2-8° C., 25° C., and 40° C.) (Table 1).

TABLE 1

Stress conditions applied to reformulated ExPEC glycoconjugate formulations

| Stress | Conditions | Time Points |
|---|---|---|
| Temperature | 5° C. | 0, 4, 8, 12 weeks |
| | 25° C. | 2, 4, 8 weeks |
| | 40° C. | 1, 2, 4 weeks |
| Agitation | Vortex (1000 rpm at ambient temp) | 4 hours |
| Freeze/Thaw | −70° C. to ambient temp | 5 consecutive cycles |
| Photosensitivity | Light exposure (ICH Q1B option 2) | 200 W/m2 UV-A light (~6 hours) + 1200 klux-hr visible light (~40 hours) |

TABLE 2

Analytical package for the analysis of reformulated ExPEC glycoconjugate formulations

| Analytical Method | Purpose |
|---|---|
| Visual Inspection | Appearance and clarity |
| pH | Acidity or basicity of samples |
| Osmolality | Osmolality |
| SEC-HPLC | Purity, aggregate, cleavages |
| Reverse phase (RP)-HPLC | Purity, chemical modifications |
| Isoelectric Focusing (IEF) | Purity, chemical modifications |
| Dynamic light scattering (DLS) | Sub-visible particles |
| FlowCAM | Sub-visible particles |

Utilizing the analytics package described in Table 2, it was demonstrated that formulations containing histidine at pH 7 or potassium phosphate at pH 7 were more stable compared to other buffer-pH combinations (data not shown). Also, at extreme pH values (i.e., pH 5.0 and pH 8.0), there appears to be more aggregation of the ExPEC glycoconjugate. Additionally, it was observed that formulations containing sorbitol as a tonicity modifier were unexpectedly more stabilizing than formulations containing NaCl as the tonicity modifier. In fact, it was observed that formulations containing NaCl were not able to stabilize the ExPEC glycoconjugate against aggregation during storage at 40° C. When sorbitol was used as a tonicity modifier, aggregation of ExPEC glycoconjugate did not occur, demonstrating that sorbitol has a surprisingly stabilizing effect. Further, the aggregation at the pH extremes (i.e., pH 5.0 and pH 8.0) is reduced in sorbitol containing formulations compared to the NaCl containing formulations. This shows that sorbitol makes the formulation more robust and capable of providing a stabilizing effect for the ExPEC glycoconjugate even if pH differences occur during production.

Example 3: Formulation Evaluation for Stability

Further formulations were designed to identify the best candidate formulations with respect to stability of the ExPEC glycoconjugate. For the buffers and pH, histidine was evaluated at a pH of 6.5 and 7.0, and instead of purely potassium phosphate, a potassium/sodium phosphate buffer ($KH_2PO_4/Na_2HPO_4$) was evaluated at a pH of 6.5 and 7.0. The combination of potassium and sodium was selected based upon initial results, and better covers the local pH buffering capacity upon freeze/thaw. Potassium dominates over sodium in the preparation of the buffering system (e.g., for a 10 mM phosphate buffer with pH=7.0, we used 6.19 mM $KH_2PO_4$ and 3.81 mM $Na_2HPO_4$). As tonicity modifiers, sucrose (8% (w/v)) and sorbitol (5% (w/v)) were evaluated. Additionally, effects of addition of anti-oxidant EDTA (1 mM) or methionine (10 mM) was evaluated. It was also tested if absence of NaCl or presence of sorbitol provided the protective effect observed in example 2, by including a formulation which comprised a combination of these (each at half the concentration as compared to when these components were used individually as in example 2). All formulations contained PS80 at a concentration of 0.02% (w/v).

The different formulations were subjected the same stress conditions described in example 2. Based on the combination of the stability data, a selection step was conducted, where the performance of each formulation was evaluated and excluded based on the following criteria: (a) an additional post-peak was visible on RP-HPLC chromatogram in at least two out of three time points for each temperature; (b) the pre-peak 1 was visible/increased on a SEC-HPLC chromatogram in at least two out of three time points for each temperature; (c) an additional post-peak was visible on a SEC-HPLC chromatogram after subjected to a stress (e.g., agitation, freeze/thaw, light exposure); and (d) the pre-peak 1 was visible/increased on a SEC-HPLC after subjected to a stress (e.g., agitation, freeze/thaw, light exposure). It was found that two particular formulations, named formulations 26 and 28 herein, were capable of providing the ExPEC glycoconjugate to withstand each stress condition tested.

Formulation 26 comprised 10 mM Na/K phosphate buffer pH 7.0, 5% (w/v) sorbitol, 10 mM methionine, 0.02% (w/v) PS-80, and the ExPEC glycoconjugate.

Formulation 28 comprised 10 mM Na/K phosphate buffer pH 7.0, 8% sucrose, 1 mM EDTA, 0.02% PS-80, and the ExPEC glycoconjugate.

Surprisingly, the specific combinations of the tonicity modifier and anti-oxidant were relevant, as formulations comprising either (i) sorbitol with methionine, or (ii) sucrose with EDTA, outperformed (a) formulations wherein sorbitol was combined with EDTA, as well as (b) formulations wherein sucrose was combined with methionine, and (c) formulations wherein no anti-oxidant was present. Also surprisingly, it was found that ExPEC glycoconjugate formulations preferably do not contain sodium chloride. The formulations 26 and 28 can be varied within ranges, while still being expected to stabilize the ExPEC glycoconjugate. Table 3 provides the applicable ranges for pH and excipient concentrations for formulations 26 and 28.

TABLE 3

Ranges for pH and excipient concentrations for ExPEC glycoconjugate formulations

| Excipient | | Range | |
|---|---|---|---|
| pH | | 6.5 | 7.5 |
| K/Na Phosphate (mM) | | 5 | 20 |
| Sorbitol (%) (w/v) | | 3 | 8 |
| Sucrose (%) (w/v) | | 3 | 12 |
| Methionine (mM) | | 5 | 1.5 |
| EDTA (mM) | | 0.1 | 1.5 |
| Surfactant (%): | F-68 | 0.05 | 0.2 |
| | PS20 | 0.01 | 0.08 |
| | PS80 | 0.01 | 0.08 |

Figure 2:
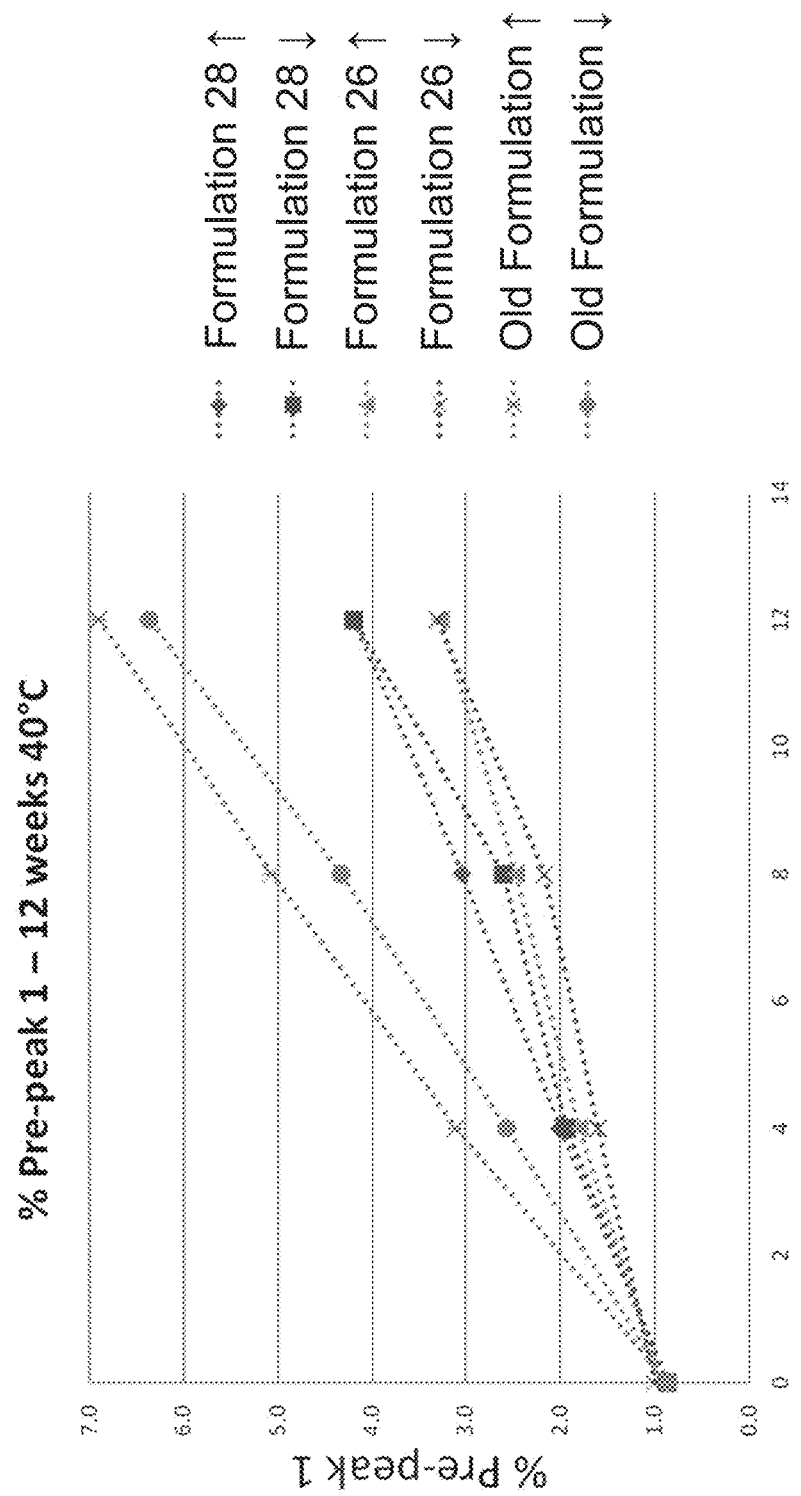
FIG. 2 shows a graph comparing percentage of SEC-HPLC chromatographic pre-peak 1 for formulations 26 and 28 head-to-head with an old ExPEC glycoconjugate formulation, when subjected to 40° C. for an extended time period of 12 weeks: both upright (↑) and inverted (↓) vial orientations were examined, Formulations 26 and 28 demonstrated increased stability over the old ExPEC glycoconjugate formulation when subjected to the thermal stress (40° C.)

Formulations 26 and 28 were further tested in a confirmation study to compare head-to-head with the old ExPEC glycoconjugate formulation (ExPEC glycoconjugate, 25 mM Tris, pH 7.4, 137 mM NaCl, 2.7 mM KCl). Both upright and inverted vial orientations were tested to assess the impact of the contact with the stopper of the final container. Formulations 26 and 28 are composed of excipients that do not pose any safety concerns at the proposed concentrations, are used in licensed vaccines and/or are listed as approved excipients for parenteral administration. The combination of these excipients for formulations 26 and 28 and the pH value of the buffering solution contribute to the improved stabilizing effect of the ExPEC glycoconjugate compared to the old ExPEC glycoconjugate formulation. The proposed combination of these excipients for formulations 26 and 28 demonstrated to preserve the drug substances (DSs) and the drug product (DP) of the ExPEC glycoconjugate vaccine upon freeze/thaw and thermal stress (e.g., FIG. 2), while complying with the expected stability trending upon storage at 2-8° C. and 25° C. (data not shown). Polysaccharide concentration tested for the DP was 20 µg/mL for each strain (80 µg/mL in total), and protein concentration was 300 µg/mL in total. For a DS of serotype O25B (i.e. containing an E. coli O25B antigen polysaccharide covalently bound to EPA carrier protein), the tested concentration of polysaccharide was 200 µg/mL and the tested concentration of protein was 830 µg/mL. Such compositions were stable over time.

So far, the drug product in formulations 26 and 28 showed stability for at least 6 months at 2-8° C., at least six months at 25° C., and stability studies are ongoing.

Example 4: Formulation Evaluation for Metal Induced Oxidation Stress

Formulations 26 and 28 were further evaluated for their stabilizing effect for the ExPEC glycoconjugate in the presence of tungsten, as a model for metal-induced product oxidation. Tungsten residues are usually present in the tip of glass pre-filled syringes (PFS), which is the result of the tip forming process with a tungsten pin. The deposition of tungsten residues in the PFS depends on the manufacturing process and can vary between PFS manufacturers in the range of 250-1250 nanograms/barrel. Tungsten has been associated with protein aggregation in PFSs (Jiang et al., J. Pharmaceutical Sci. 98(12): 4695-710 (2009); Seidl et al., Pharmaceutical Res. 29:1454-67 (2012)). Thus, the stability of formulations 26 and 28 and the old formulation were investigated when exposed to tungsten at different concentrations while monitoring oxidative stress and propensity of aggregation of the ExPEC glycoconjugate. In this evaluation, three levels of tungsten (high (HW), medium (MW), and low (LW)) were examined covering all the levels of tungsten residue present in PFS available currently in the market. The stress conditions applied to the formulations are summarized in Table 4.

TABLE 4

Stress conditions applied to tungsten containing formulations

| Stress | Conditions | Time Points |
|---|---|---|
| Temperature | 40° C. | 0, 1, 2, and 4 weeks |
| Agitation | Vortex (200 rpm at ambient temp) | 24 hours |

Figure 3A:
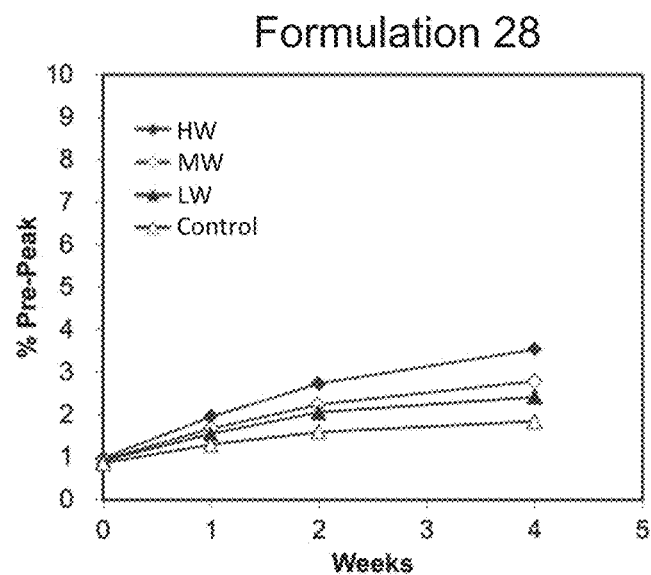
FIGS. 3A, 3B and 3C show graphs demonstrating the pre-peak 1 trends for formulations 26 and 28 as compared to the old ExPEC glycoconjugate formulation when exposed to three different concentrations of tungsten extract (HW, MW, LW) and stored at 40° C. for 4 weeks.
Figure 3B:
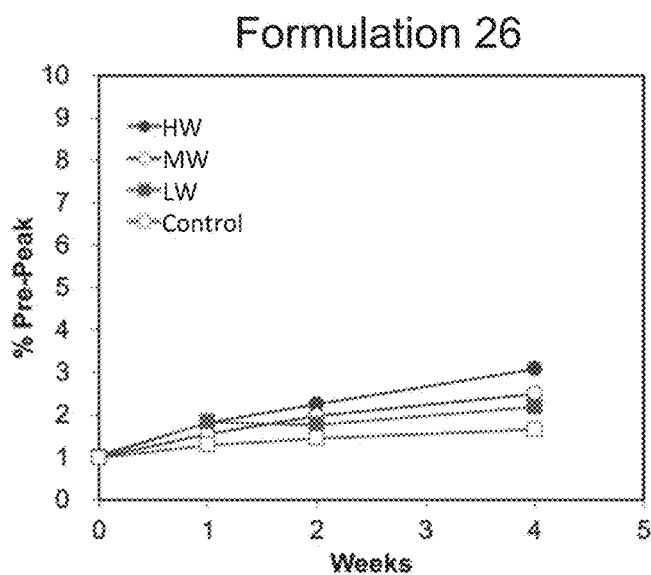
Figure 3C:
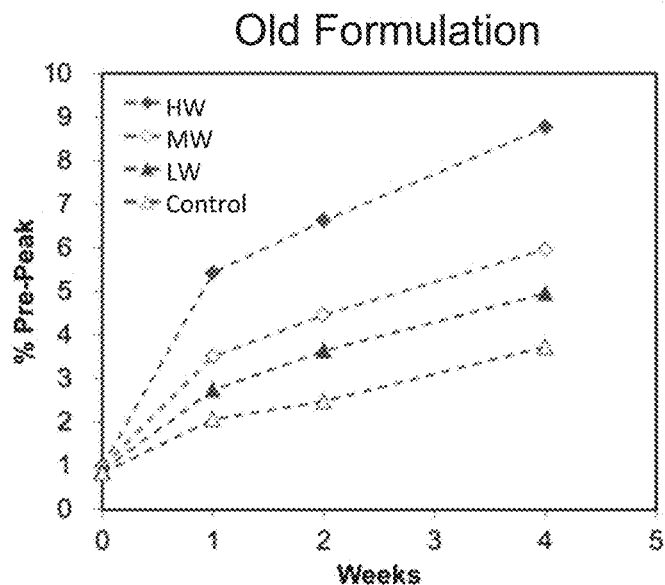

Formulations 26 and 28 were shown to have the least amount of aggregates of the ExPEC glycoconjugate over time, as demonstrated by SEC-HPLC analysis (stability-indicating pre-peak 1). Pre-peak levels at 4 weeks only reached 3.1% as compared to 1.0% at T-0, even when exposed to the highest levels of tungsten (averaging 0.5% growth per week, FIGS. 3A, 3B and 3C).

The invention thus provides two different improved liquid formulations for ExPEC glycoconjugate vaccine. The first, most preferred, composition comprises the ExPEC glycoconjugate, sorbitol, methionine, K/Na-phosphate buffer pH 7 and surfactant. The second preferred composition comprises the ExPEC glycoconjugate, sucrose, EDTA, K/Na-phosphate buffer pH 7 and surfactant. These compositions have the advantage over the previously described composition that upon storage at 2-8° C., the ExPEC glycoconjugate vaccine shows a better stability profile in the new formulations of the invention, where aggregation and degradation product formation is prevented, as shown by stability indicating assays (SEC-HPLC and RP-HPLC). The stabilizing effect of both new invented formulations is even more evident upon freeze/thaw, thermal (40° C.), and metal induced oxidation stress when analyzed with the aforementioned analytical techniques. These features allow multiple storage and transportation options for both DS and DP for ExPEC glycoconjugate vaccine. In addition, the improved properties with regards to withstanding metal-induced oxidation stress, could also be applied in long term storage of the ExPEC vaccine in alternative primary packaging systems (e.g. prefilled syringe and/or applicable devices).

Example 5: Formulation Evaluation for Compatibility with Plastic Materials

Figure 4:
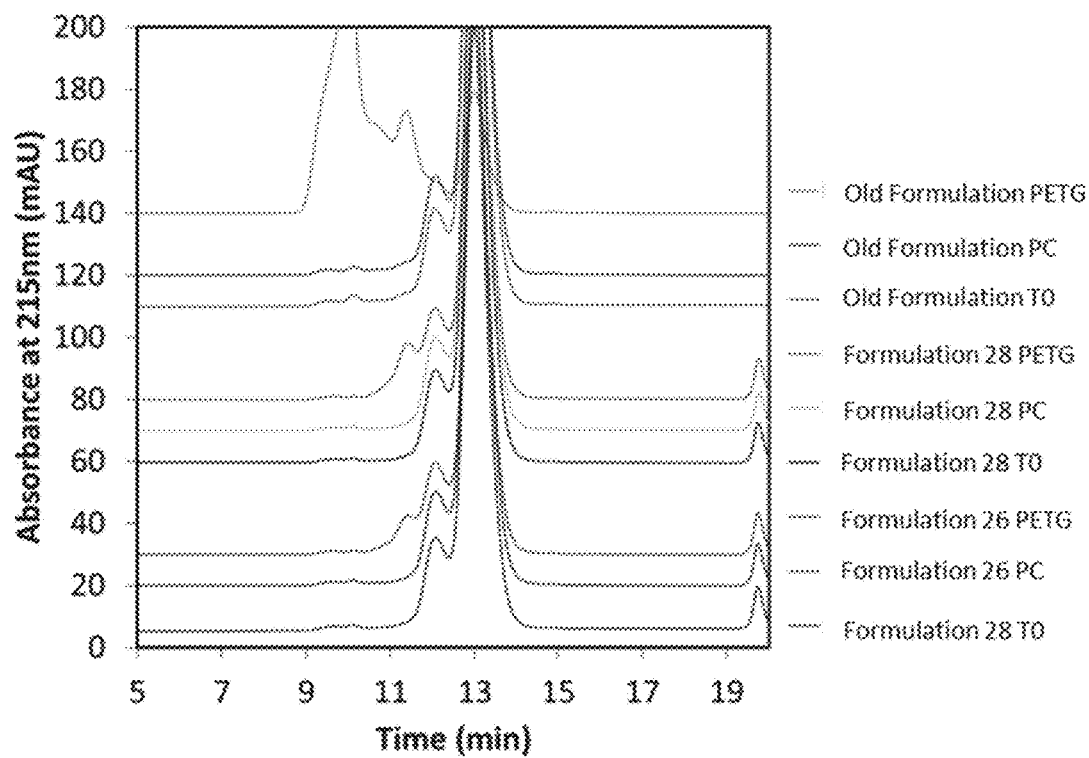
FIG. 4 shows SEC-HPLC chromatograms demonstrating the results of the experiment before and after agitation stress (T0 is control, i.e. no agitation stress) for formulation 26 and 26 as compared to the old formulation in contact with PETG and PC plastic materials.

Formulations 26 and 28 were further evaluated for their stabilizing effect for the ExPEC glycoconjugate drug substance (O25B conjugate, tested concentration of polysaccharide 227-242 µg/mL and protein 952-1048 µg/mL) in contact with various plastic materials such as polycarbonate (PC) and polyethylene terephthalate glycol (PETG). Plastic materials have been associated with protein degradation, e.g. when the plastic material had been sterilized by irradiation. The formulations were tested for stability under harsh agitation stress (24 hours at 200 rpm at room temperature) in PETG and PC containers. The old formulation demonstrated complete degradation under these conditions in the PETG container. In contrast, as demonstrated by SEC-HPLC analysis (see FIG. 4, using pre-peak 1 as an indicator for instability), formulations 26 and 28 remained stable under the same conditions in the tested PETG and PC containers. In addition, stability of the drug substance in these formulations stored for seven days in PC and PETG containers at 25° C. was observed (data not shown).

What is claimed is:

1. A composition comprising:
   (a) at least one O-antigen polysaccharide covalently bound to a carrier protein;
   (b) 3% to 8% (w/v) sorbitol;
   (c) 5 to 15 mM methionine;
   (d) 5 to 20 mM phosphate buffer comprising potassium phosphate and sodium phosphate at a pH of 6.5 to 7.5;
   (e) 0.01% to 0.2% (w/v) surfactant; and
   (f) water.

2. The composition of claim 1, wherein the at least one 0-antigen polysaccharide comprises an E. coli O25B antigen polysaccharide.

3. The composition of claim 1, wherein the concentration of sorbitol is 5% (w/v).

4. The composition of claim 1, wherein the concentration of methionine is 10 mM.

5. The composition of claim 1, wherein the concentration of the phosphate buffer is 10 mM, and the pH of the phosphate buffer is 7.0.

6. The composition of claim 1, wherein the surfactant is polysorbate 80 (PS80).

7. The composition of claim 1, wherein the surfactant is selected from the group consisting of poloxamer 188, polysorbate 20 (PS20), and polysorbate 80 (PS80).

8. The composition of claim 1, which is stable for at least 6 months when stored at a temperature of 2-8° C.

9. The composition of claim 1, comprising two or more 0-antigen polysaccharides, wherein the concentration of each of the 0-antigen polysaccharides is independently about 1 to 200 µg/mL.

10. The composition of claim 1, wherein the O-antigen polysaccharide to carrier protein weight/weight ratio is 1:10 to 1:2 for each O-antigen polysaccharide.

11. The composition of claim 1, which is stable for at least 6 months when stored at a temperature of −18° C. to −80° C.

12. The composition of claim 1, comprising a concentration of total 0-antigen polysaccharide of 4 to 1000 µg/mL.

13. The composition of claim 1, comprising a total concentration of carrier protein of 40 to 2000 µg/mL.

14. The composition of claim 1, in a container made of glass, polycarbonate, or polyethylene terephthalate.

15. A composition comprising:
   (a) at least one 0-antigen polysaccharide covalently bound to a carrier protein;
   (b) 5% (w/v) sorbitol;
   (c) 10 mM methionine;
   (d) 10 mM phosphate buffer comprising $KH_2PO_4$ and $Na_2HPO_4$ at a pH of 7.0;
   (e) 0.02% (w/v) polysorbate 80 (PS80); and
   (f) water.

16. A method of preparing a composition according to claim 1, the method comprising mixing:
   (a) at least one O-antigen polysaccharide covalently bound to a carrier protein;
   (b) sorbitol;
   (c) methionine;
   (d) phosphate buffer comprising potassium phosphate and sodium phosphate at a pH of 6.5 to 7.5;
   (e) surfactant; and
   (f) water,
to thereby prepare the composition.

17. The method according to claim 16, further comprising storing the composition at a temperature of 2-8° C. for at least 6 months.

18. The method according to claim 16, further comprising storing the composition at a temperature of −18° C. to −80° C. for at least 6 months.

19. A method for stably maintaining an E. coli O25B-antigen polysaccharide in a liquid composition, comprising preparing the liquid composition and storing the liquid composition at a temperature of 2-8° C., wherein the liquid composition comprises:
   (a) 1 to 200 µg/mL of the E. coli O25B-antigen polysaccharide covalently bound to a carrier protein;
   (b) 3% to 8% (w/v) sorbitol;
   (c) 5 to 15 mM methionine;
   (d) 5 to 20 mM phosphate buffer comprising potassium phosphate and sodium phosphate at a pH of 6.5 to 7.5;
   (e) 0.01% to 0.2% (w/v) surfactant, and
   (f) water.

20. The method of claim 19, wherein the liquid composition further comprises one or more additional E. coli O-antigen polysaccharides covalently bound to a carrier protein.

21. The composition of claim 1, in a vial.

22. The composition of claim 1, in a syringe.

* * * * *

SEQUENCE LISTING

<160> NUMBER OF SEQ ID NOS: 2

<210> SEQ ID NO 1
<211> LENGTH: 612
<212> TYPE: PRT
<213> ORGANISM: Artificial Sequence
<220> FEATURE:
<223> OTHER INFORMATION: detoxified exotoxin A of Pseudomonas aeruginosa

<400> SEQUENCE: 1

Ala Glu Glu Ala Phe Asp Leu Trp Asn Glu Cys Ala Lys Ala Cys Val
1 5 10 15

Leu Asp Leu Lys Asp Gly Val Arg Ser Ser Arg Met Ser Val Asp Pro
20 25 30

Ala Ile Ala Asp Thr Asn Gly Gln Gly Val Leu His Tyr Ser Met Val
35 40 45

Leu Glu Gly Gly Asn Asp Ala Leu Lys Leu Ala Ile Asp Asn Ala Leu
50 55 60

Ser Ile Thr Ser Asp Gly Leu Thr Ile Arg Leu Glu Gly Gly Val Glu
65 70 75 80

Pro Asn Lys Pro Val Arg Tyr Ser Tyr Thr Arg Gln Ala Arg Gly Ser
85 90 95

Trp Ser Leu Asn Trp Leu Val Pro Ile Gly His Glu Lys Pro Ser Asn
100 105 110

Ile Lys Val Phe Ile His Glu Leu Asn Ala Gly Asn Gln Leu Ser His
115 120 125

Met Ser Pro Ile Tyr Thr Ile Glu Met Gly Asp Glu Leu Leu Ala Lys
130 135 140

Leu Ala Arg Asp Ala Thr Phe Phe Val Arg Ala His Glu Ser Asn Glu
145 150 155 160

Met Gln Pro Thr Leu Ala Ile Ser His Ala Gly Val Ser Val Val Met
165 170 175

Ala Gln Ala Gln Pro Arg Arg Glu Lys Arg Trp Ser Glu Trp Ala Ser
180 185 190

Gly Lys Val Leu Cys Leu Leu Asp Pro Leu Asp Gly Val Tyr Asn Tyr
195 200 205

Leu Ala Gln Gln Arg Cys Asn Leu Asp Asp Thr Trp Glu Gly Lys Ile
210 215 220

Tyr Arg Val Leu Ala Gly Asn Pro Ala Lys His Asp Leu Asp Ile Lys
225 230 235 240

Pro Thr Val Ile Ser His Arg Leu His Phe Pro Glu Gly Gly Ser Leu
245 250 255

Ala Ala Leu Thr Ala His Gln Ala Cys His Leu Pro Leu Glu Ala Phe
260 265 270

Thr Arg His Arg Gln Pro Arg Gly Trp Glu Gln Leu Glu Gln Cys Gly
275 280 285

Tyr Pro Val Gln Arg Leu Val Ala Leu Tyr Leu Ala Ala Arg Leu Ser
290 295 300

Trp Asn Gln Val Asp Gln Val Ile Arg Asn Ala Leu Ala Ser Pro Gly
305 310 315 320

Ser Gly Gly Asp Leu Gly Glu Ala Ile Arg Glu Gln Pro Glu Gln Ala
325 330 335

Arg Leu Ala Leu Thr Leu Ala Ala Ala Glu Ser Glu Arg Phe Val Arg
340 345 350

Gln Gly Thr Gly Asn Asp Glu Ala Gly Ala Ala Ser Ala Asp Val Val

```
                    355                 360                 365
Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Trp Ser Leu Pro Gly Phe Tyr
            500                 505                 510

Arg Thr Gly Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Val Thr Ile Leu Gly Trp Pro Leu Ala
545                 550                 555                 560

Glu Arg Thr Val Val Ile Pro Ser Ala Ile Pro Thr Asp Pro Arg Asn
                565                 570                 575

Val Gly Gly Asp Leu Asp Pro Ser Ser Ile Pro Asp Lys Glu Gln Ala
            580                 585                 590

Ile Ser Ala Leu Pro Asp Tyr Ala Ser Gln Pro Gly Lys Pro Pro Arg
        595                 600                 605

Glu Asp Leu Lys
    610

<210> SEQ ID NO 2
<211> LENGTH: 5
<212> TYPE: PRT
<213> ORGANISM: Artificial Sequence
<220> FEATURE:
<223> OTHER INFORMATION: preferred N-linked glycosylation consensus
      sequence
<220> FEATURE:
<221> NAME/KEY: MISC_FEATURE
<222> LOCATION: (1)..(1)
<223> OTHER INFORMATION: Xaa can be Asp or Glu
<220> FEATURE:
<221> NAME/KEY: MISC_FEATURE
<222> LOCATION: (2)..(2)
<223> OTHER INFORMATION: Xaa can be any amino acid except Pro
<220> FEATURE:
<221> NAME/KEY: MISC_FEATURE
<222> LOCATION: (4)..(4)
<223> OTHER INFORMATION: Xaa can be any amino acid except Pro
<220> FEATURE:
<221> NAME/KEY: MISC_FEATURE
```

```
<222> LOCATION: (5)..(5)
<223> OTHER INFORMATION: Xaa can be Ser or Thr

<400> SEQUENCE: 2

Xaa Xaa Asn Xaa Xaa
1               5
```